United States Patent [19]

Dieter et al.

[11] Patent Number: 5,405,847

[45] Date of Patent: Apr. 11, 1995

[54] 4,5-DIHYDRO-4-OXO-PYRROLO[1,2-A]QUINOXALINONES AND CORRESPONDING AZA ANALOGS AND A PROCESS FOR THEIR PREPARATION

[75] Inventors: Hans-Reinhold Dieter, Darmstadt; Jürgen Engel, Alzenau; Karl-Heinz Klingler, Langen; Bernhard Kutscher, Maintal; Stefan Szelenyi, Schwaig; Ute Achterath-Tuckermann, Maintal; Jürgen Schmidt; Peter Metzenauer, both of Gründau, all of Germany

[73] Assignee: Asta Medica Aktiengesellschaft, Dresden, Germany

[21] Appl. No.: 110,957

[22] Filed: Aug. 24, 1993

[30] Foreign Application Priority Data

Aug. 24, 1992 [DE] Germany .............. 42 28 095.8

[51] Int. Cl.⁶ ............... A61K 31/505; A61K 31/535; C07D 471/14; C07D 487/14

[52] U.S. Cl. ..................... 514/250; 544/115; 544/344; 544/346

[58] Field of Search ............ 544/344, 346, 115; 514/250

[56] References Cited

U.S. PATENT DOCUMENTS

4,151,280 4/1979 Rowlands et al. ............ 544/344
4,446,323 5/1984 Freed et al. ............ 544/344

FOREIGN PATENT DOCUMENTS

0070518 1/1983 European Pat. Off. .
0344943 12/1989 European Pat. Off. .
0368652 5/1990 European Pat. Off. .
0400583 12/1990 European Pat. Off. .
2816109 10/1978 Germany .

OTHER PUBLICATIONS

Davey et al. (J. Med. Chem. (1991), 34 2671–2677).
Ager, (J. Med. Chem (1988), 31 1098–1115).
Adegoke (J. Heterocycl. Chem. 19 (1982) 1169–72).

Nagarajan et al., Indian Journal of Chemistry, 1972, 10(4):344–350.

*Primary Examiner*—Mukund J. Shah
*Assistant Examiner*—Matthew V. Grumbling
*Attorney, Agent, or Firm*—Cushman, Darby & Cushman

[57] ABSTRACT

Novel compounds of the formula

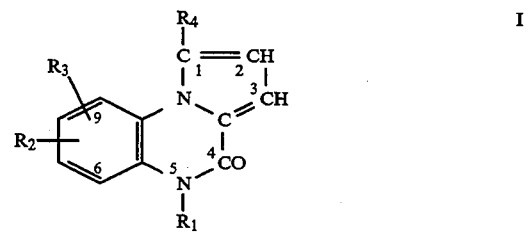

where the phenyl ring can also contain a nitrogen atom instead of a CH group, $R_1$ is $C_2$–$C_6$-alkenyl, $C_2$–$C_6$-alkynyl, hydroxy, $C_1$–$C_6$-alkoxy, $C_3$–$C_6$-alkenyloxy, $C_3$–$C_6$-alkynyloxy, $C_2$–$C_6$-alkanoyloxy, benzoyloxy, morpholinocarbonyloxy, $C_1$–$C_6$-alkyloxycarbonyloxy, $C_1$–$C_6$-alkylaminocarbonyloxy, $C_1$–$C_6$-dialkylaminocarbonyloxy or the group -Alk-A, where Alk represents $C_1$–$C_6$-alkyl, $C_2$–$C_6$-hydroxyalkyl or $C_3$–$C_6$-cycloalkyl and the symbol A represents hydrogen or other substituents.

$R_2$, $R_3$ and $R_4$ represent various substituents, where $R_1$ may also be hydrogen, when $R_2$ is the group

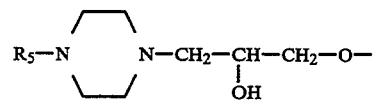

and $R_5$ represents phenyl, $C_1$–$C_4$-alkoxyphenyl or diphenylmethyl and $R_3$ and $R_4$ are hydrogen and their salts. The compounds provide anti-allergic, anti-asthmatic, anxiolytic and hypotensive effects.

1 Claim, No Drawings

4,5-DIHYDRO-4-OXO-PYRROLO[1,2-A]QUINOXALINONES AND CORRESPONDING AZA ANALOGS AND A PROCESS FOR THEIR PREPARATION

The present invention relates to

BACKGROUND OF THE INVENTION

European patent application 0 400 583 relates to imidazoquinoxalinones and their aza analogs of the following general formula:

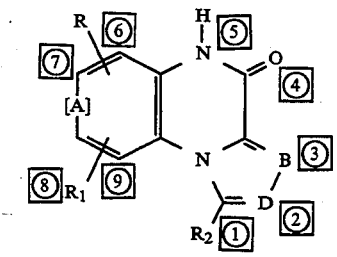

where A is a nitrogen atom or CH, B and D are a nitrogen atom or CH, B and D are a nitrogen atom or CH is a substituted carbon atom and the radicals R, $R_1$ and $R_2$ represent hydrogen or various organic substituents.

These compounds are said to have a positive inotropic vessel dilating effect. In addition, the Indian Journal of Chemistry, Volume 10, 1972, pages 344–350 describe inter alia the preparation of compounds of Formula:

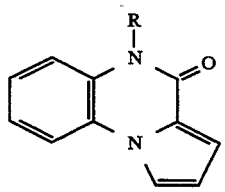

where the radical R can be 3-dimethylaminopropyl-(1), 2-morpholinoethyl-(1), 2-pyrrolidinoethyl-(1) or 2-dimethylaminoethyl-(1). No pharmacological effect is described.

SUMMARY OF THE INVENTION

The invention relates to Compounds of the formula:

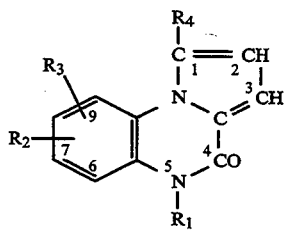

I where the phenyl ring can also contain a nitrogen atom instead of a CH group either in position 6, 7, 8 or 9 and the radicals $R_1$, $R_2$, $R_3$ and $R_4$ have the following meanings:

$R_1$: $C_2$–$C_6$-alkenyl, $C_2$–$C_6$-alkynyl, hydroxy, $C_1$–$C_6$-alkoxy, $C_3$–$C_6$-alkenyloxy, $C_3$–$C_6$-alkynyloxy, $C_2$–$C_6$-alkanoyloxy, benzoyloxy, morpholinocarbonyloxy, $C_1$–$C_6$-alkyloxycarbonyloxy, $C_1$–$C_6$-alkylaminocarbonyloxy, $C_1$–$C_6$-dialkylaminocarbonyloxy or the group -Alk-A where Alk: is $C_1$–$C_6$-alkyl, $C_2$–$C_6$-hydroxyalkyl or $C_3$–$C_6$-cycloalkyl and the symbol A represents:

1. Hydrogen, halogen, hydroxy, $C_1$–$C_6$-alkoxy, $C_2$–$C_6$-alkanoyloxy, phenyl;
2. —$NHR_5$, —$NR_5R_6$, $NR_5R_6R_7$, pyridylamino, imidazolyl, pyrrolidinyl, N—$C_1$–$C_6$-alkylpyrrolidinyl, piperidylamino, N-(phenyl-$C_1$–$C_4$-alkyl)-piperidylamino where $R_5$ and $R_6$ may be the same or different and represent hydrogen, $C_1$–$C_6$-alkyl, $C_3$–$C_7$-cycloalkyl, $C_3$–$C_7$-hydroxycycloalkyl, morpholino-$C_1$–$C_6$-alkyl, phenyl, phenyl-$C_1$–$C_6$-alkyl or phenyl-$C_2$–$C_6$-oxyalkyl, it also being possible for the phenyl radicals to be substituted by halogen and $R_7$ is hydrogen or $C_1$–$C_6$-alkyl;
3. The group:

-CO-D where D is phenyl, $C_1$–$C_6$-alkyl, $C_3$–$C_7$-cycloalkyl, hydroxy, $C_1$–$C_6$-alkoxy, $C_3$–$C_7$-cycloalkyloxy, morpholino, pyrrolidino, piperidino, homopiperidino, piperazino, —$NHR_5$ or —$NR_5R_6$ and $R_5$ and $R_6$ have the meanings given.

4. The group

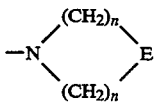

where n can be the integers 1-3 and E represents $CH_2$, oxygen, sulfur, NH, CHOH, CH—$C_1$–$C_6$-alkyloxy, CH—$C_2$–$C_6$-alkanoyloxy, CHC$_6$H$_5$, CHCOD, CH—$CH_2C_6H_5$, N—$C_1$–$C_6$-alkyl, N—$C_1$–$C_6$-hydroxyalkyl, N—$C_6H_5$, N—$CH_2C_6H_5$, N—CH ($C_6$-$H_5$)$_2$, N—($CH_2$)$_2$—OH, N—($CH_2$)$_3$—OH or NCOD and the phenyl radicals ($C_6H_5$) may also be substituted by halogen, $C_1$–$C_6$-alkoxy, trifluoromethyl, $C_1$–$C_6$-alkyl, methylenedioxy, cyan and D has the meanings given above;

$R_2$ and $R_3$, which may be the same or different: hydrogen, halogen, hydroxy, $C_1$–$C_6$-alkyl, trifluoromethyl, —CN, $C_1$–$C_6$-alkoxy, $C_3$–$C_6$-alkenyloxy, $C_3$–$C_6$-alkinyloxy, —$NHR_5$, —$NR_5R_6$, $NR_5R_6R_7$ (meanings $R_5$, $R_6$, $R_7$ as given) or the group -G-Alk-A, where Alk and A have the meanings given and G is oxygen, sulfur, NH or $NR_5$;

$R_4$: hydrogen or halogen, where $R_1$ can also be hydrogen, when $R_2$ is the group

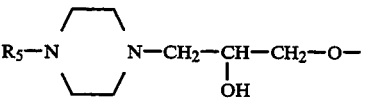

and $R_5$ represents phenyl, $C_1$–$C_4$-alkoxyphenyl or diphenylmethyl and $R_3$ and $R_4$ are hydrogen, and their physiologically acceptable acid addition salts and quaternary ammonium salts, with the exception of the compounds of Formula I where $R_1$ is methyl, dimethylaminopropyl, dimethylaminoethyl, morpholinoethyl or pyrrolidinoethyl, $R_2$, $R_3$ and $R_4$ are hydrogen and the phenyl ring does not contain a nitrogen atom.

The novel compounds of the invention are pharmacologically active and have, in particular, anti-allergic and anti-asthmatic effects, anxiolytic effects, hypotensive effects (for example selective $\alpha_2$-blockade), vasodilatory effects (inodilatory) and a positive inotropic effect (selective PDE-III-inhibition).

It is an object of the invention to provide novel compounds with favorable and improved pharmacological properties.

The invention also relates to a novel improved process for the preparation of compounds of Formula I, where $R_1$ and $R_4$ are hydrogen and the radicals $R_2$ and $R_3$ are the same or different and represent hydrogen, halogen, $C_1$–$C_6$-alkyl, —$CF_3$, —CN, $C_1$–$C_6$-alkoxy, amino, $C_2$–$C_6$-alkanoylamino, —$NO_2$, hydroxy, —$SO_3H$, —$CO_2H$, —COO—$C_1$–$C_6$-alkyl, CONH—$C_1$–$C_6$-alkyl, CON($C_1$–$C_6$-alkyl)$_2$, —$NHR_2$ or $NR_5R_6$, where $R_5$ and $R_6$ have the meanings given above. More specifically, the invention provides a process for the preparation of compounds of the formula I:

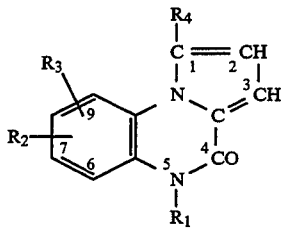

where the phenyl ring can also contain a nitrogen atom instead of a CH group in either 6, 7, 8 or 9 position and the radicals $R_1$, $R_2$, $R_3$ and $R_4$ have the following meanings:

$R_1$: $C_2$–$C_6$-alkenyl, $C_2$–$C_6$-alkynyl, hydroxy, $C_1$–$C_6$-alkoxy, $C_3$–$C_6$-alkenyloxy, $C_3$–$C_6$-alkynyloxy, $C_2$–$C_6$-alkanoyloxy, benzoyloxy, morpholinocarbonyloxy, $C_1$–$C_6$-alkyloxycarbonyloxy, $C_1$–$C_6$-alkylaminocarbonyloxy, $C_1$–$C_6$-dialkylaminocarbonyloxy or the group -Alk-A where Alk: $C_1$–$C_6$-alkyl, $C_2$–$C_6$-hydroxyalkyl or $C_3$–$C_6$-cycloalkyl and the symbol A represents:

1. Hydrogen, halogen, hydroxy, $C_1$–$C_6$-alkoxy, $C_2$–$C_6$-alkanoyloxy, phenyl;
2. —$NHR_5$, —$NR_5R_6$, $NR_5R_6R_7$, pyridylamino, imidazolyl, pyrrolidinyl, N—$C_1$–$C_6$-alkylpyrrolidinyl, piperidylamino, N-(phenyl-$C_1$–$C_4$-alkyl)-piperidylamino where $R_5$ and $R_6$ may be the same or different and represent hydrogen, $C_1$–$C_6$-alkyl, $C_3$–$C_7$-cycloalkyl, $C_3$–$C_7$-hydroxycycloalkyl, morpholino-$C_1$–$C_6$-alkyl, phenyl, phenyl-$C_1$–$C_6$-alkyl or phenyl-$C_2$–$C_6$-oxyalkyl, it also being possible for the phenyl radicals to be substituted by halogen and $R_7$ is hydrogen or $C_1$–$C_6$-alkyl;
3. The group:

-CO-D where D is phenyl, $C_1$–$C_6$-alkyl, $C_3$–$C_7$-cycloalkyl, hydroxy, $C_1$–$C_6$-alkoxy, $C_3$–$C_7$-cycloalkyloxy, morpholino, pyrrolidino, piperidino, homopiperidino, piperazino, —$NHR_5$ or —$NR_5R_6$ and $R_5$ and $R_6$ have the meanings given.

4. The group

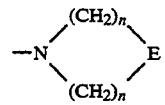

where n can be the integers 1–3 and E represents $CH_2$, oxygen, sulfur, NH, CHOH, CH—$C_1$–$C_6$-alkyloxy, CH—$C_2$–$C_6$-alkanoyloxy, $CHC_6H_5$, CHCOD, CH—$CH_2C_6H_5$, N—$C_1$–$C_6$-alkyl, N—$C_1$–$C_6$-hydroxyalkyl, N—$C_6H_5$, N—$CH_2C_6H_5$, N—CH($C_6$–$H_5$)$_2$, N—($CH_2$)$_2$—OH, N—($CH_2$)$_3$—OH or NCOD and the phenyl radicals ($C_6H_5$) may also be substituted by halogen, $C_1$–$C_6$-alkoxy, trifluoromethyl, $C_1$–$C_6$-alkyl, methylenedioxy, cyan and D has the meanings given above;

$R_2$ and $R_3$, which may be the same or different: hydrogen, halogen, hydroxy, $C_1$–$C_6$-alkyl, trifluoromethyl, —CN, $C_1$–$C_6$-alkoxy, $C_3$–$C_6$-alkenyloxy, $C_3$–$C_6$-alkynyloxy, —$NHR_5$, —$NR_5R_6$, $NR_5R_6R_7$ (meanings $R_5$, $R_6$, $R_7$ as given) or the group -G-Alk-A, where Alk and A have the meanings given and G is oxygen, sulfur, NH or $NR_5$;

$R_4$: hydrogen or halogen, where $R_1$ can also be hydrogen, when $R_2$ is the group

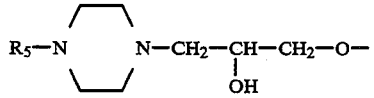

and $R_5$ represents phenyl, $C_1$–$C_4$-alkoxyphenyl or diphenylmethyl and $R_3$ and $R_4$ are hydrogen, and their physiologically acceptable acid addition salts and quaternary ammonium salts, with the exception of the compounds of Formula I where $R_1$ is methyl, dimethylaminopropyl, dimethylaminoethyl, morpholinoethyl or pyrrolidinoethyl, $R_2$, $R_3$ and $R_4$ are hydrogen and the phenyl ring does not contain a nitrogen atom. In the method of the invention, the radical $R_1$ is introduced into a compound of the formula:

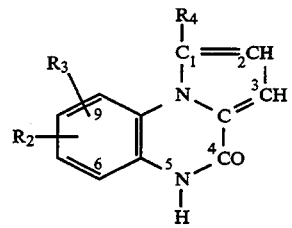

where $R_2$, $R_3$ and $R_4$ can have the meanings given above by reaction with a compound $R_1$Hal, where $R_1$ has the meanings given above, apart from the hydroxy group, and/or the group Alk-A is introduced into a compound of Formula II, in which $R_2$ is hydroxy, $R_3$ and $R_4$ have the meanings given by reaction with a compound Hal-Alk-A, the compounds obtained are optionally alkylated, acylated, aminated and/or if $R_1$ is a $C_1$–$C_6$-alkoxy group, splits off the alkylether group to the hydroxy group for purposes of completion of the radicals $R_2$ and $R_3$ and also $R_1$ and optionally converts the compounds obtained into their salts, The invention also provides a process for the preparation of compounds of formula

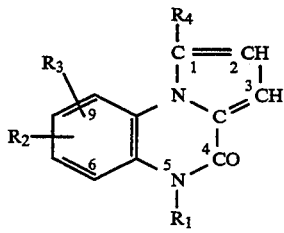

I where the phenyl ring can also contain a nitrogen atom in the 9 position instead of a CH group and the radicals $R_1$, $R_2$ and $R_3$ have the following meanings:

$R_1$: hydrogen $R_2$, $R_3$ (the same or different: hydrogen, halogen, $C_1$-$C_6$-alkyl, $CF_3$, —CN, $C_1$-$C_6$-alkoxy, amino, $C_2$-$C_6$-alkanoylamino, —$NO_2$, hydroxy, —$SO_3H$ —$CO_2H$, —COO—$C_1$-$C_6$-alkyl, —CONH—$C_1$-$C_6$-alkyl, —CON ($C_1$-$C_6$-alkyl)$_2$, —$NHR_5$ or —$NR_5R_6$, where $R_5$ and $R_6$ have the meanings given above. In this method, a compound of formula III:

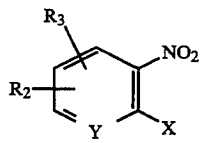

III where $R_2$ and $R_3$ have the meanings previously given, Y represents a nitrogen atom or CH and X is fluorine, chlorine, bromine or iodine is reacted with a compound of the formula IV:

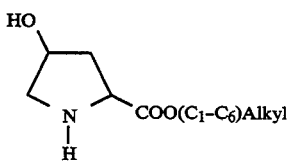

IV to a compound of the formula V:

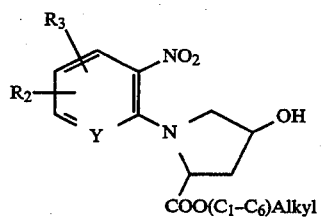

V

This compound is reacted by reduction to a compound of formula VI:

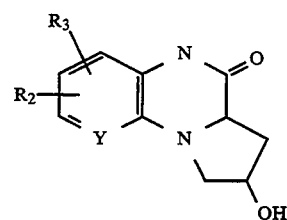

VI and the compound of formula VII:

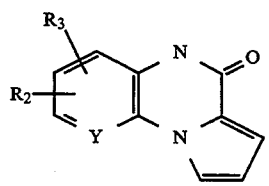

VII is obtained from the compound so obtained by treatment with oxygen or an oxygen-supplying substance.

The following remarks provide important information by way of example:

The alkyl groups, halogenalkyl groups, alkenyl groups, alkynyl groups, alkoxy groups, alkylamino groups, alkanoylamino groups, alkanoyloxy groups or quite generally alkanoyl groups can be straight or branched. The same also applies to the alkyl and alkyloxy groups (=alkoxy groups) where these are components of groups of different composition (for example in the form of a monoalkyl- or dialkylamino group, alkanoylamino group, alkoxycarbonylamino group, carbalkoxy group and analogous groups.

The $C_3$-$C_7$-cycloalkyl group is preferably cyclopentyl or cyclohexyl. $C_2$-$C_6$-alkenyl preferably means propenyl. $C_2$-$C_6$-alkinyl preferably means propinyl.

The halogen atoms are chlorine, bromine or fluorine, in particular chlorine and fluorine. The alkyl and alkoxy groups as such, or as a constituent of differently composed groups, contain, in particular, 1–4 carbon atoms, preferably 1 or 2 carbon atoms. Alkanoyl groups, such as alkanoylamino groups or alkanoyloxy groups contain, in particular, 2–4, preferably 2–3 carbon atoms. Alk consists in particular of 1–4, preferably 2–3 carbon atoms.

The compounds of Formula I are preferably compounds where the radicals $R_1$, $R_2$, $R_3$ and $R_4$ have the following meanings:

$R_1$: hydrogen, $C_1$-$C_6$-alkyl or the group

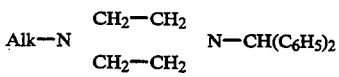

where one or both phenyl radicals can also be substituted by halogen, in particular fluorine.

$R_2$: hydrogen, $C_1$-$C_6$-alkoxy or the group G-Alk-A, where G is oxygen, Alk consists of 2–4 carbon atoms and A is the group CO—$NR_5R_6$ where $R_5$=$C_1$-$C_4$-alkyl and $R_6$=$C_4$-$C_7$-cycloalkyl.

The radical $R_2$ is preferably located in 8-position. $R_3$ and $R_4$: hydrogen Particularly favorable properties are, for example, displayed by the following compounds of Formula I:

D 21247 (Example 1), D 19897 (Example 12), D 20971 (Example 28), D 20467,

D 20972 (Example 29), D 20469,
D 20896 (Example 11), D 20354.

D 20354 = 4,5-dihydro-8-[2-hydroxy-3-(4-(2-methoxyphenyl) piperazine-1-yl)-propyloxy]-4-oxo-pyrido[3,2-e]pyrrolo[1,2-a]pyrazine hydrochloride D 20467 = 4,5-dihydro-8-[2-hydroxy-3-(4-benzhydrylpiperazine-1-yl)-propyloxy]-4-oxo-pyrido[3,2-e]pyrrolo[1,2-a]pyrazine dihydrochloride monohydrate D 20469 = 4,5-dihydro-8-[2-hydroxy-3-(4-phenyl-piperidine-1-yl)-propyloxy]-4-oxo-pyrido[3,2-e]pyrrolo[1,2 -a]pyrazine hydrochloride Those compounds of Formula I which contain asymmetrical carbon atoms and generally occur as racemates can be split in a manner known per se, for example using an optically active acid, into the optically active isomers. It is, however, also possible to use an optically active starting material from the outset, a correspondingly optically active or diastereomeric form then being obtained as end product. The instant invention thus also covers the D- and L-form as well as the DL-mixture in the event that the compound of Formula I contains an asymmetrical carbon atom and in the event of 2 and more asymmetrical carbon atoms also the corresponding diastereomeric forms.

Depending on the conditions of the process and starting materials, the end products of Formula I are either obtained in free form or in the form of their salts. The salts of the end products can be transformed into the bases in a manner known per se, for example using alkali or ion exchangers. Salts may be obtained from the latter by reaction with organic or inorganic acids, in particular those suitable for the formation of therapeutically acceptable salts.

The compounds of the invention are suitable for the preparation of pharmaceutical compositions. The pharmaceutical compositions or medications can contain one or several of the compounds of the invention. Conventional carriers and auxiliary substances may be used to prepare the pharmaceutical formulations.

With reference to the first process described above, the process may be carried out without solvent or in a suitable solvent or dispersing agent. Solvents or dispersing agents that may for example be considered are: aromatic hydrocarbons such as benzene, mesitylene, toluene, xylene; pyridine; lower aliphatic ketones such as acetone, methyl ethyl ketone; halogenated hydrocarbons such as chloroform, 1,2-dichloroethane, tetrahydrocarbon, chlorobenzene, methylene chloride; ethers such as tetrahydrofuran, dioxane, diisopropyl ether; sulfoxides such as dimethyl sulfoxide; tertiary acid amides such as dimethyl formamide, dimethyl acetamide, hexamethyl phosphoric acid triamide, tetramethyl urea, N-methyl pyrrolidone; lower alcohols such as methanol, ethanol, isopropanol, amyl alcohol, butanol, tert. butanol as well as mixtures of the agents named, optionally also with water.

It is recommended that the reaction be carried out under a protective gas atmosphere. Protective gases that may for example be considered are: nitrogen, argon.

The reaction is for example conducted at temperatures between 20° and 200° C., preferably 40° to 160° C. or also 50° to 120° C.

If a solvent or dispersing agent is used, the process is often carried out at the reflux temperature of this agent. The reaction frequently occurs at room temperature or at a temperature between 40° and 120° C.

In the case of the starting component $R_1Hal$, Hal preferably represents chlorine, bromine or iodine. This also applies to the starting component Hal-Alk-A.

The reaction preferably takes place in the presence of acid binding agents such as alkali carbonates (potassium carbonate, sodium carbonate), alkali acetates, alkali hydroxides or tertiary bases (triethylamine, pyridine).

The starting compound II is preferably used in the form of its metal salt. It is in particular possible to use the alkali salts (Na, K, Li). The alkali salts are for example prepared using the corresponding alkali hydrides, alkali amides, alkali alcoholates or also alkali metals in a solvent (lower alcohol, aromatic hydrocarbon) or with aqueous alkali (for example NaOH).

Alkylation, acylation and amination particularly involves the acylation or alkylation of amino groups and-/or hydroxy groups or the replacement of a halogen atom by $NH_2$ or alkylsubstituted amino. The alkylation or acylation is for example effected by reaction with compounds of the formula R-Hal, $ArSO_2OR$ and $SO_2$-$(OR)_2$, where Hal is a halogen atom (in particular chlorine, bromine or iodine) and Ar is an aromatic radical (for example a phenyl or naphthyl radical, optionally substituted by one or several lower alkyl radicals, and R is for example the radicals $C_1$-$C_6$-alkyl, $C_2$-$C_6$-alkenyl, $C_2$-$C_6$-alkinyl, $C_2$-$C_6$-alkanoyl, bezoyl, morpholinocarbonyl, $C_1$-$C_6$-alkyloxycarbonyl, $C_1$-$C_6$-alkylaminocarbonyl, $C_1$-$C_6$-dialkylaminocarbonyl, the group COD (meanings of D as given above) or Ar-$C_1$-$C_6$-alkyl.

Examples are corresponding p-toluenesulfonic acid alkyl esters, corresponding dialkyl sulfates, corresponding alkyl halides and the like. The alkylation and acylation reaction is optionally carried out with addition of conventional acid-binding agents, such as alkali hydroxides, alkali carbonates, alkali hydrocarbonates, alkali hydrogen carbonates, alkaline earth carbonates, alkaline earth acetates, tertiary amines (for example trialkylamine such as triethylamine), pyridine or also alkalihydrides at temperatures between 0° and 200° C., preferably 40° and 140° C. in inert solvents or suspension agents. Solvents or dispersing agents that may for example be considered are: aromatic hydrocarbons such as benzene, toluene, xylene; aliphatic ketones such as acetone, methylethyl ketone; halogenated hydrocarbons such as chloroform, carbon tetrachloride, chlorobenzene, methylene chloride, aliphatic ethers such as butyl ether; cyclic ethers such as tetrahydrofuran, dioxane; sulfoxides such as dimethyl sulfoxide; tertiary acid amides such as dimethyl formamide, N-methylpyrrolidone, hexamethylphosphoric acid triamide; aliphatic alcohols such as methanol, ethanol, isopropanol, amyl alcohol, tert.-butanol, cycloaliphatic hydrocarbons such as cyclohexane and the like. It is also possible to use aqueous mixtures of the solvents named. The process is often carried out at the reflux temperature of the solvents or dispersing agents used. The alkylation reaction components are often used in excess. The alkylation can also be carried out in the presence of tetraalkylammonium salts (in particular the halides) in combination with alkalihydroxides at temperatures between 0°–100° C., preferably 20°–80° C., in an aprotic solvent or also in chloroform or methylene chloride. Aprotic solvents that may in particular be considered are: tertiary amides (dimethyl formamide, N-methyl-pyrrolidone, hexamethylphosphoric acid triamide), dimethyl sulfoxide, acetonitrile, dimethoxyethane, acetone, tetrahydrofuran.

During acylation the group —COD (meanings of D as given above), the group —CO—$C_1$-$C_6$-alkyl, benzoyl or the $C_1$–$C_6$-alkoxycarbonyl group are for example introduced into amino groups or hydroxy groups. The process is carried out in a manner known per se, using for example the corresponding acid halides (chloride, bromide) such as carb—$C_1$–$C_6$-alkoxyhalides or corresponding anhydrides). The reaction temperatures are preferably between 30° and 120° C.

It is optionally also possible to proceed during alkylation and acylation by first preparing an alkali compound (sodium, potassium or also lithium salt for example) from the compound to be alkylated or acylated by reacting them in an inert solvent such as dioxane, dimethylformamide, benzene or toluene with an alkali metal, alkali hydride or alkali amide (in particular sodium or sodium compounds) or butyl lithium at temperatures between 0° and 150° C. and then adding the alkylating agent.

Instead of the alkylating and acylating agents listed it is also possible to use chemically equivalent agents conventionally used in chemistry (see for example also L. F. and Mary Fieser "Reagents for Organic Synthesis", John Wiley and Sons, Inc., New York, 1967, Vol. 1, pages 1303–4 and Vol. 2, page 471.

Acyl groups present, such as carb-$C_1$–$C_6$-alkoxy groups, $C_2$–$C_6$-alkanoyl groups and similar groups can be split off solvolytically. This splitting is effected in known manner, for example by saponification with acids (mineral acids such as hydrochloric acid, sulfuric acid, in particular concentrated hydrohalic acids such as HBr/glacial acetic acid) or using base substances (potashes, soda, aqueous alkali solutions, alcoholic alkali solutions, aqueous $NH_3$) at temperatures between 10° and 150° C., in particular 20°–100° C. The amidation involves the reaction of a halogenalkyl function (for example $R_1$ is Alk-A and/or $R_2$, $R_3$ are G-Alk-A, where A is a halogen atom such as chlorine, bromine or iodine) with —$NHR_5$, —$NR_5R_6$, $NR_5R_6R_7$, pyridyl amino, imidazolyl, pyrrolidinyl, N—$C_1$–$C_6$-alkylpyrrolidinyl, piperidylamino, N-(phenyl-$C_1$–$C_4$-alkyl)-piperidylamino, where $R_5$ and $R_6$ are the same or different and represent hydrogen, $C_1$–$C_6$-alkyl, $C_3$–$C_7$-cycloalkyl, $C_3$–$C_7$-hydroxycycloalkyl, morpholino-$C_1$–$C_6$-alkyl, phenyl, phenyl-$C_1$–$C_6$-alkyl or phenyl-$C_2$–$C_6$-oxyalkyl, where the phenyl radicals may also be substituted by halogen and $R_7$ is hydrogen or $C_1$–$C_6$-alkyl, or the reaction of a halogenalkyl function of this type with amines of the following formula

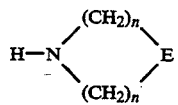

where n can be the integers 1–3 and E can represent $CH_2$, oxygen, sulfur, NH, CHOH, CH—$C_1$–$C_6$-alkyloxy, CH—$C_2$–$C_3$-alkanoyloxy, CH$C_6H_5$, CHCOD, CH—$CH_2C_6H_5$, N—$C_1$–$C_6$-alkyl, N—$C_1$–$C_6$-hydroxyalkyl, N—$C_6H_5$, N—$CH_2C_6H_5$, N—CH($C_6H_5$)$_2$, N—$(CH_2)_2$—OH, N—$(CH_2)_3$—OH or NCOD and the phenyl radicals ($C_6H_5$) may also be substituted by halogen, $C_1$–$C_6$-alkoxy, trifluoromethyl, $C_6$–$C_6$-alkyl, methylenedioxy, cyan and D is phenyl, $C_1$–$C_6$-alkyl, $C_3$–$C_7$-cycloalkyl, hydroxy, $C_1$–$C_6$-alkoxy, $C_3$–$C_7$-cycloalkyloxy, morpholino, pyrrolidino, piperidino, homopiperidino, piperazino, —$NHR_5$ or —$NR_5R_6$ and $R_5$ and $R_6$ have the meanings given. This reaction occurs under the conditions given for the first process described above.

The splitting off of ether groups occurs for example without solvent or in an inert solvent such as boron tribromide, boron trifluoride, aluminum chloride, silicon tetrachloride, aluminium tribromide, sodium ethylthiolate, $(CH_3)_3SiCl+NaI$ at temperatures between −70° C. and 200° C. Solvents that may for example be used for this ether splitting are: aliphatic hydrogen halides such as methylene chloride, aromatic hydrocarbons such as benzene, toluene, xylene, halogenated aromatic hydrocarbons such as chlorobenzene, dichlorobenzene, dimethylformamide, acetonitrile.

This ether splitting may also occur using hydriodic acid, muriatic acid (for example alcoholic HCl), pyridine hydrochloride, hydrobromic acid, methyl magnesium iodide with or without solvent at temperatures between 0° C. to 150° C. Solvents for the last-named splitting that may for example be considered are aliphatic ethers with alkyl radicals of 1 to 6 carbon atoms, water.

Details on the reaction conditions and reaction components of the above named reactions are also given in the instructions for the preparation of the starting materials.

The reaction of a compound III with the compound IV occurs in a solvent or suspension agent (lower aliphatic alcohols, dimethylsulfoxide, water and aqueous mixtures) at temperatures between 10° and 150° C., preferably 20°–80° C. The process is appropriately carried out in the presence of basic substances such as alkali carbonates, tertiary aliphatic amines, pyridine. Preparation of compound VI by reductive treatment of compound V.

Catalytic hydration has proved particularly suitable for this reduction. Catalysts that may for example be considered are: Raney nickel, precious metals such as palladium and platinum as well as compounds thereof, with and without carriers, such as for example coal, barium sulfate, calcium sulfate and so on. It is advisable to carry out the hydration of the nitro group at temperatures between 20° and 100° C. and a pressure of about 1 to 70 bar in a solvent. Solvents that may for example be used are $C_1$–$C_4$-alkanols, $C_2$–$C_4$-diols and their lower alkyl ethers, cyclic ethers such as dioxane, tetrahydrofuran, methoxyethanol, water, aromatic hydrocarbons (benzene, toluenes, xylols) as well as mixtures of these agents. It may in some cases be advantageous for the subsequent isolation of the reduced compounds if drying agents such as anhydrous sodium or magnesium sulfate are added at the beginning to the mixture to be hydrated.

The reduction may, however, also be carried out with nascent hydrogen, for example zinc/hydrochloric acid, tin/hydrochloric acid, iron/hydrochloric acid, iron/glacial acetic acid or with salts of hydrogen sulphide in alcohol/water at about 70° to about 120° C. or with activated aluminum in aqueous ether at 20° to 40° C. or with tinII-chloride/hydrochloric acid or with ammonium formate. Detailed explanation of the second novel process of the invention described above: General synthesis instructions for the preparation of N-aryl- or N-pyridyl-2-ethoxycarbonyl-4-hydroxypyrolidines (compounds of Formula V)

Process variant A

A mixture of 1 Mol of the appropriate o-halogen nitroaromatic substances, 234.8 g (1.2 Mol) L-4-hydroxyproline ethylester hydrochloride and 414.6 g (3 Mol) potassium carbonate in 2 liters ethanol is heated with stirring for 20–120 hours to 50°–60° C. After cooling to room temperature, insoluble constituents are filtered off and the reaction mixture is concentrated in a vacuum. The remaining oily residue is taken up in 1 l dichloromethane and extracted once in each case with 400 ml semi-concentrated hydrochloric acid and 200 ml water. The organic phase is dried with calcium chloride and then concentrated in a vacuum. After drying in a vacuum the corresponding N-aryl- or N-pyridyl-2-ethoxycarbonyl-4-hydroxypyrrolidines are obtained in 65–95 percent yield and are generally used in the next step of the process without further purification.

Process variant B

A mixture of 1Mol of the appropriate o-halogen nitroaromatic compounds, 157.4 g (1.2 Mol) L-4-hydroxyproline and 202.4 g (2 Mol) triethylamine in 1.5 liters dimethylsulfoxide is heated with stirring for 20–120 hours to 50°–70° C. After cooling to room temperature, the reaction mixture is mixed with 4.5 liters water and the resultant solution is extracted twice with in each case 500 ml ether. The ether extract is discarded and the aqueous phase is adjusted to a pH=2–3 with concentrated hydrochloric acid. The aqueous phase is then extracted four times with, in each case, 750 ml dichloromethane. The combined dichloromethane extracts are dried with sodium sulfate and then concentrated in a vacuum. After drying in a vacuum the corresponding N-aryl- or N-pyridyl-2-carboxy-4-hydroxypyrrolidines are obtained in 65–95 percent yield and are generally used in the next step of the process without further purification.

The following were for example prepared according to variant A:
2-[1-(2-ethoxycarbonyl-4-hydroxy)pyrrolidinyl]-6-methoxy-3-nitropyridine: orange-yellow oil.
1-[1-(2-ethoxycarbonyl-4-hydroxy)pyrrolidinyl]-2nitrobenzene: orange-yellow oil. General synthesis instructions for the preparation of annellated pyrrolo[1,2-a]-pyrazinones (compounds of Formula VI) and their oxidation to compounds of Formula VII Process variant A A solution of 0.5 Mol of the corresponding o-[1-(2-ethoxycarbonyl-4-hydroxy)-pyrrolidinyl]-nitroaromatic compounds or o-[1-(2-carboxy-4-hydroxy)pyrrolidinyl]-nitroaromatic compounds in 1.5 liters methanol is hydrated in the presence of palladium on active charcoal under normal pressure at approx. 60° C. When hydrogen uptake is completed the catalyst is filtered off, the filtrate is diluted with 3 liters methanol, acidulated with methanolic hydrochloric acid (pH=1–2) and the resultant solution is stirred with passage of air for 1–5 days at room temperature. The solution is concentrated in a vacuum to approx. 300 ml and allowed to crystallize overnight at 0°–4° C. The precipitated crystals are suction filtered, rewashed with 100 ml methanol and dried in a vacuum.

Process variant B

A solution of 0.5 Mol of the corresponding 0-[1-(2-ethoxy-carbonyl-4-hydroxy)-pyrrolidinyl]-nitroaromatic compounds or o-[1-(2-carboxy-4-hydroxy)-pyrrolidinyl]-nitroaromatic compounds in 1 liter glacial acetic acid is mixed in portions with stirring and nitrogen atmosphere with 75 g iron powder. When addition has been completed, the reaction mixture is heated for 3–5 hours to 60°–70° C. After cooling to room temperature, insoluble constituents are filtered off and the filtrate is evaporated to dryness in a vacuum. The remaining residue is exhaustively extracted with dichloromethane. The methylene chloride phase is concentrated in a vacuum, the residue taken up in 3 liters methanol and the arsenate solution is acidulated with methanolic hydrochloric acid (pH=1–2). The mixture is then stirred at room temperature for 1–5 days with passage of air. The reaction solution is concentrated to about 300 ml and caused to crystallize overnight at 0°–4° C. The crystals are suctioned off, rewashed with methanol and dried in a vacuum.

The following compounds were for example obtained according to variant A:
4,5-dihydro-8-methoxy]-4-oxo-pyrido[3,2-e]pyrrolo[1,2-a]pyrazine (number D 17500).
Colorless to beige crystals, M.P. 274°–276° C.
4,5-dihydro-4-oxo-pyrrolo[1,2-a]quinoxalinone (number D 18543).
Colorless to beige crystals, M.P. 271°–273° C.
4,5-dihydro-4-oxo-pyrido[3,2-e]pyrrolo[1,2-a]pyrazine (number D 18367).
Colorless to beige crystals, M.P. 281°–284° C.
8-chloro-4,5-dihydro-4-oxo-pyrido[3,2-e]pyrrolo[1,2-a]pyrazine (number D 18370).
Colorless to beige crystals, M.P. 297°–299° C.
4,5-dihydro-8-methyl-4-oxo-pyrrolo[1,2a]quinoxalinone (number D 19786).
Colorless to beige crystals, M.P. 283°–285° C.
The following were for example obtained according to variant B:
4,5-Dihydro-7-methyl-4-oxo-pyrrolo[1,2-a]quinoxalinone (number D 19777).
Colorless to beige crystals, M.P. 258° C.
7-Amino-4,5-dihydro-4-oxo-pyrrolo[1,2-a]quinoxalinone hydrochloride (number D 19457).
Dark beige crystals, M.P. 324°–328° C.
4,5-Dihydro-7-trifluoromethyl-4-oxo-pyrrolo[1,2-a]-quinoxalinone (number D 19801).
Colorless to beige crystals, M.P. 240°–241° C.
4,5-Dihydro-8-fluoro-4-oxo-pyrrolo[1,2-a]quinoxalinone (number D 19823).
Colorless to beige crystals, M.P. 318° C.
4,5-Dihydro-7-fluoro-4-oxo-pyrrolo[1,2-a]quinoxalinone (number D 19857).
Colorless to beige crystals, M.P. 281° C.
9-Chloro-4,5-dihydro-4-oxo-pyrrolo[1,2-a]quinoxalinone (number D 19858).
Colorless to beige crystals, M.P. 309° C.
7-Cyano-4,5-dihydro-4-oxo-pyrrolo[1,2-a]quinoxalinone (number D 20353)
Colorless to beige crystals, M.P. 312° C.
The starting materials for the preparation of the compounds of the invention are known or can be prepared according to the second novel process described above, and/or by analogy with the following examples.

EXAMPLE I 4,5-Dihydro-8-hydroxy-4-oxo-pyrido[3,2-e]pyrrolo[1,2-a]pyrazine (number D 19459).

A mixture of 107.6 g (0.5 Mol) 4,5-dihydro-8-methoxy-4-oxo- pyrido[3,2-e]pyrrolo[1,2-a]pyrazine and 2 liters 48 percent aqueous hydrobromic acid is heated with stirring under a protective gas atmosphere for 5 hours until reflux. After cooling to room temperature the precipitated product is suctioned off and washed with 500 ml water. The solid material is taken up in 1000 ml water and the resultant suspension adjusted until alkaline (pH 10) with stirring using concentrated ammonia. The solvent is filtered off and the filter cake is heated in 1000 ml ethanol with stirring for 1 hour until reflux. After cooling the solid material is suctioned off, rewashed with 200 ml ethanol and dried in a vacuum. 87.9 g 4,5-dihydro-8-hydroxy-4-oxo-pyrido[3,2-e]pyrrolo[1,2-a]pyrazine are obtained as beige-colored crystals, M.P. 364°–368° C.

EXAMPLE II 4,5-Dihydro-8-[2-hydroxy-3-(4-(2-methoxyphenyl)-piperazine-1-yl)-propyloxy]-4-oxo-pyrido[3,2-e]-pyrrolo[1,2-a]pyrazine hydrochloride (number D 20354).

A suspension of 4.0 g (20 mmol) 4,5-dihydro-8-hydroxy-4-oxo-pyrido[3,2-e]pyrrolo[1,2-a]pyrazine in 65 ml dimethylformamide is reacted with stirring and exclusion of moisture in portions with 0.8 g (20 mmol) 80 percent sodium hydride in white oil. When addition has been completed the mixture is stirred for 2 hours at room temperature and then a solution of 5.7 g (20 mmol) 1-(3-chloro-2-hydroxypropyl)-4-(2-methoxyphenyl)-piperazine in 30 ml dimethylformamide is added dropwise with stirring under a protective gas atmosphere. When addition has been completed, the mixture is gradually heated to approx. 100°–110° C. and allowed to post-react at this temperature for 3 hours. After cooling to room temperature, insoluble constituents are filtered off, and the filtrate is evaporated to dryness in a vacuum. The remaining residue is taken up in ethanol and the solution resulting after filtration is acidulated with ethanolic hydrochloric acid (pH 2). The precipitated solid material is suctioned off and recrystallized from an ethanol/water mixture. After drying in a vacuum, 3.8 g of the above cited compound D 20354 are obtained as beige-colored crystals, M.P. 251°–255° C.

The following compounds are obtained by analogy:

4,5-Dihydro-8-[2-(4-(2-fluorophenylpiperazine-1-yl)ethoxy]-4-oxo-pyrido[3,2-e]pyrrolo[1,2-a]pyrazine hydrochloride (number D 20366).

4.0 g (20 mmol) 4,5-Dihydro-8-hydroxy-4-oxo-pyrido[3,2-e]pyrrolo[1,2-a]pyrazine are reacted by analogy with Example II with 4.6 g (20 mmol) 1-(2-chloroethyl)-4-(2-fluorophenyl) piperazine and appropriately worked up. 1.5 g of substance D 20366 are obtained as beige-colored crystals, M.P.>260° C.

8-[3-(4-(3-chlorophenylpiperazine-1-yl)-propyloxy-4,5-dihydro-4-oxo-pyrido[3,2-e]pyrrolo[1,2-a]pyrazine hydrochloride (number D 20367).

4.0 g (20 mmol) 4,5-Dihydro-8-hydroxy-4-oxo-pyrido[3,2-e]pyrrolo[1,2-a]pyrazine are reacted by analogy with Example II with 5.5 g (20 mmol) 1-(3-chloropropyl)-4-(3-chlorophenyl) piperazine and appropriately worked up. 4.1 g of substance D 20367 are obtained as beige-colored crystals, M.P.>260° C.

4,5-Dihydro-8-[3-(4-(2-fluorophenylpiperazine-1-yl)propyloxy]-4-oxo-pyrido[3,2-e]pyrrolo[1,2-a]pyrazine hydrochloride (number D 20368).

4.0 g (20 mmol) 4,5-Dihydro-8-hydroxy-4-oxo-pyrido[3,2-e]pyrrolo[1,2-a]pyrazine are reacted by analogy with Example II with 5.1 g (20 mmol) 1-(3-chloropropyl)-4-(2-fluorophenyl) piperazine and appropriately worked up. 2.1 g of substance D 20368 are obtained as beige-colored crystals, M.P.>260° C.

4,5-Dihydro-8-[2-(4-(2-nitrophenylpiperazine-1-yl)-ethoxy]-4-oxo-pyrido[3,2-e]pyrrolo[1,2-a]pyrazine hydrochloride (number D 20369).

4.0 g (20 mmol) 4,5-Dihydro-8-hydroxy-4-oxo-pyrido[3,2-e]pyrrolo[1,2-a]pyrazine are reacted by analogy with Example II with 5.4 g (20 mmol) 1-(2-chloroethyl)-4-(2-nitrophenyl)piperazine and appropriately worked up. 2.4 g of substance D 20369 are obtained as beige-colored crystals, M.P.>260° C.

4,5-Dihydro-8-[2-hydroxy-3-(4-phenylpiperazine-1-yl)-propyl oxy]-4-oxo-pyrido[3,2 -e]pyrrolo[1,2-a]pyrazine hydrochloride (number D 20381).

4.0 g (20 mmol) 4,5-Dihydro-8-hydroxy-4-oxo-pyrido[3,2-e]pyrrolo[1,2-a]pyrazine are reacted by analogy with Example II with 5.1 g (20 mmol) 1-(2-chloroethyl)-4-phenyl) piperazine and appropriately worked up. 1.7 g of substance D 20381 are obtained as beige-colored crystals, M.P.>260° C.

4,5-Dihydro-8-[2-(4-phenylpiperazine-1-yl)-ethoxy]-4-oxo-pyrido[3,2-e]pyrrolo[1,2-a]pyrazine hydrochloride monohydrate (number D 20391).

4.0 g (20 mmol) 4,5-Dihydro-8-hydroxy-4-oxo-pyrido[3,2-e]pyrrolo[1,2-a]pyrazine are reacted by analogy with Example II with 4.5 g (20 mmol) 1-(2-chloroethyl)-4-phenyl) piperazine and appropriately worked up. 2.2 g of substance D 20391 are obtained as beige-colored crystals, M.P.>260° C.

4,5-Dihydro-8-[2-(4-(3-chlorophenyl)piperazine-1-yl)-ethoxy]-4-oxo-pyrido[3,2-e]pyrrolo[1,2-a]pyrazine hydrochloride monohydrate (number D 20408).

4.0 g (20 mmol) 4,5-Dihydro-8-hydroxy-4-oxo-pyrido[3,2-e]pyrrolo[1,2-a]pyrazine are reacted by analogy with Example II with 4.9 g (20 mmol) 1-(2-chloroethyl)-4-(3-chlorophenyl)-piperazine and appropriately worked up. 2.9 g of substance D 20408 are obtained as beige-colored crystals, M.P.>260° C.

4,5-Dihydro-8-[2-(4-(2-aminophenyl)piperazine-1-yl)-ethoxy]-4-oxo-pyrido[3,2-e]pyrrolo[1,2-a]pyrazine dihydrochloride monohydrate (number D 20409).

4.0 g (20 mmol) 4,5-Dihydro-8-hydroxy-4-oxo-pyrido[3,2-e]pyrrolo[1,2-a]pyrazine are reacted by analogy with Example II with 4.2 g (20 mmol) 1-(2-chloroethyl)-4-(2-aminophenyl)-piperazine and appropriately worked up. 1.5 g of substance D 20409 are obtained as beige-colored crystals, M.P.>260° C.

4,5-Dihydro-8-[2-hydroxy-3-(4-(2-methylphenyl)-piperazine-1-yl)-propyloxy]-4-oxo-pyrido[3,2-e]pyrrolo[1,2-a]pyrazine hydrochloride (number D 20410).

4.0 g (20 mmol) 4,5-Dihydro-8-hydroxy-4-oxo-pyrido[3,2-e]pyrrolo[1,2-a]pyrazine are reacted by analogy with Example II with 5.4 g (20 mmol) 1-(3-chloro-2-hydroxypropyl-4-(2-methylphenyl)-piperazine and appropriately worked up. 1.7 g of substance D 20410 are obtained as beige-colored crystals, M.P>260° C.

4,5-Dihydro-8-[3-(4-benzylpiperazine-1-yl)-propyloxy]-4-oxo-pyrido[3,2-e]pyrrolo[1,2-a]pyrazine hydrochloride (number D 20426).

4.0 g (20 mmol) 4,5-Dihydro-8-hydroxy-4-oxo-pyrido[3,2-e]pyrrolo[1,2-a]pyrazine are reacted by analogy with Example II with 4.5 g (20 mmol) 1-(3-chloropropyl)-4-benzylpiperazine and appropriately worked up. 2.3 g of substance D 20426 are obtained as beige-colored crystals, M.P.>260° C.

4,5-Dihydro-8-[2-hydroxy-3-(4-benzhydrylpiperazine-1-yl)-propyloxy]-4-oxo-pyrido[3,2-e]pyrrolo[1,2-a]pyrazine dihydrochloride monohydrate (number D 20467).

4.0 g (20 mmol) 4,5-Dihydro-8-hydroxy-4-oxo-pyrido[3,2-e]pyrrolo [1,2-a]pyrazine are reacted by analogy with Example II with 6.9 g (20 mmol) 4-benzhydryl-1-(3-chloro-2-hydroxypropyl)-piperazine and appropriately worked up. 3.8 g of substance D 20467 are obtained as beige-colored crystals, M.P. >260° C.

4,5-Dihydro-8-[2-hydroxy-3-(4-benzylpiperazine-1-yl)-propyloxy]-4-oxo-pyrido[3,2-e]pyrrolo[1,2-a]pyrazine dihydrochloride monohydrate (number D 20468).

4.0 g (20 mmol) 4,5-Dihydro-8-hydroxy-4-oxo-pyrido[3,2-e]pyrrolo[1,2-a]pyrazine are reacted by analogy with Example II with 4.8 g (20 mmol) 4-benzyl-1-(3-chloro-2-hydroxypropyl)-piperazine and appropriately worked up. 2.6 g of substance D 20468 are obtained as beige-colored crystals, M.P. >260° C.

4,5-Dihydro-8-[2-hydroxy-3-(4-phenylpiperidine-1-yl)-propyloxy-]-4-oxo-pyrido[3,2-e]pyrrolo[1,2-a]pyrazine hydrochloride (number D 20469).

4.0 g (20 mmol) 4,5-Dihydro-8-hydroxy-4-oxo-pyrido[3,2-e]pyrrolo[1,2-a]pyrazine are reacted by analogy with Example II with 5.1 g (20 mmol) 1-(3-chloro-2-hydroxypropyl)-4-phenylpiperidine and appropriately worked up. 3.0 g of substance D 20469 are obtained as beige-colored crystals, M.P. >260° C.

4,5-Dihydro-8-[2-(4-(2-methoxyphenyl)piperazine-1-yl)-propyloxy-4-oxo-pyrido[3,2-e]pyrrolo[1,2-a]pyrazine hydrochloride (number D 20214).

4.0 g (20 mmol) 4,5-Dihydro-8-hydroxy-4-oxo- pyrido[3,2-e]pyrrolo[1,2-a]pyrazine are reacted by analogy with Example II with 5.1 g (20 mmol) 1-(2-chloroethyl)-4-(2-methoxyphenyl)-piperazine and appropriately worked up. 3.2 g of substance D 20214 are obtained as beige-colored crystals, M.P. >260°-262° C.

4,5-Dihydro-8-[3-(4-(2-methoxyphenyl)piperazine-1-yl)-propyloxy]-4-oxo-pyrido[3,2-e]pyrrolo[1,2-a]pyrazine hydrochloride (number D 20215).

4.0 g (20 mmol) 4,5-Dihydro-8-hydroxy-4-oxo-pyrido[3,2-e]pyrrolo[1,2-a]pyrazine are reacted by analogy with Example II with 5.4 g (20 mmol) 1-(3-chloropropyl)-4-(2-methoxyphenyl)-piperazine and appropriately worked up. 4.1 g of substance D 20215 are obtained as beige-colored crystals, M.P. >265°-267° C.

4,5-Dihydro-8-[ethoxycarbonyl-methoxy]-4-oxo-pyrido[3,2-e]pyrrolo]1,2-a]pyrazine (number D 19919).

4.0 g (20 mmol) 4,5-Dihydro-8-hydroxy-4-oxo-pyrido[3,2-e]pyrrolo[1,2-a]pyrazine are reacted by analogy with Example II with 2.5 g (20 mmol) chloroacetic acid ethyl ester and appropriately worked up. 1.8 g of substance D 19919 are obtained as colorless crystals, M.P. >198°-199° C.

4,5-Dihydro-8-[3-ethoxycarbonyl-butyloxy]-4-oxo-pyrido[3,2-e]pyrrolo[1,2-a]pyrazine (number D 19937).

4.0 g (20 mmol) 4,5-Dihydro-8-hydroxy-4-oxo-pyrido[3,2-e]pyrrolo[1,2-a]pyrazine are reacted by analogy with Example II with 3.9 g (20 mmol) 5-bromovaleric acid ethyl ester and appropriately worked up. 2.8 g of substance D 19937 are obtained as colorless crystals, M.P. >147°-149° C.

In vivo in various asthma models and in vitro in the inhibition of mediator release, the compounds of the invention display a good anti-allergic, anti-asthmatic and anti-inflammatory effect as well as a good effect also for example in psoriasis and properties related therewith.

The minimum effective dose in the above cited animal experiment is for example
10 mg/kg oral
0.1 mg/kg intravenous
1 mg/kg inhalative The general dose range for the effect (animal experiment as above) that may for example be considered is:
10–100 mg/kg oral, in particular 20–50 mg/kg
0.1–10 mg/kg intravenous, in particular 0.3–0.5 mg/kg
1–30 mg/kg inhalative, in particular 5–15 mg/ml The direction of effect of the compounds of the invention is comparable with the effect of the known medicamentous active substance DNCG, although the following differences exist in particular thereto: more potent, other mediators besides histamine are inhibited.

Indications for which the compounds of the invention may be considered are: asthma, allergic rhinitis, rheumatoid arthritis, psoriasis, Morbus Crohn, Colitis ulcerosa.

The pharmaceutical formulations generally contain between 0.01% and 10%, preferably 0.1% to 1%, of the active component(s) of the invention.

Administration may for example be in the form of tablets, capsules, pills, coated tablets, suppositories, ointments, gels, creams, powders, dusting powders, aerosols or in liquid form. Liquid forms of application that may for example be considered are: oily or alcoholic or aqueous solutions as well as suspensions and emulsions. Preferred forms of administration are solutions containing between 0.01 and 10 percent by weight of active substance.

The individual dose of the active components of the invention may for example be:
a) for oral medicinal forms, between 10–100 mg/kg, preferably 20–50 mg/kg.
b) for parenteral forms (for example intravenous, intramuscular) between 0.1–10 mg/kg, preferably 0.2–0.5 mg/kg.
c) for medicinal forms for inhalation (solutions or aerosols) between 1 mg/ml–30 mg/ml, preferably 5–15 mg/ml.

(The doses are in each case related to the free base).

It is, for example, possible to recommend 1 tablet containing 230 to 2400 mg active substance, 3 times daily or for example in intravenous injection one ampoule of 1 to 5 ml content with 7 to 70 mg substance, once daily. In the case of oral administration the minimum daily dose is, for example, 700 mg; the maximum daily dose in oral administration should not exceed 7 g.

The acute toxicity of the compounds of the invention in the mouse (expressed by the LD 50 mg/kg; method after Miller and Tainter: Proc. Soc. Exper. Biol. a. Med. 57 (1944) 261) is for example above 1000 mg/kg in oral application. More detailed information on the previously mentioned test models. The figures cited relate to the compounds of the invention, in particular the compounds according to Example I.

In vivo

1. Ovalbumin-induced asthmatic late phase eosinophilia in the lung (guinea pigs)
Lit.: Lung, 169, 1991, p. 227–240
5 mg/kg/i.p.: 67% inhibition
10 mg/kg/i.p.: 98% inhibition
2. Asthma-induced by domestic dust mites (rabbits)

Lit.: J. Allergy Clin. Immunol. 87, 1991, p. 312 Administration/dosage: 10 mg/ml as aerosol for 2 minutes
Bronchoconstriction: 49% inhibition
Asthmatic late phase: 51% inhibition
Bronchial hyperreactivity: 51% inhibition
3. Allergic bronchoconstriction according to Konzett-Rössler (rat)
  Lit.: Naunyn-Schmiedeb. Arch. Exp. Pathol. Pharmakol. 195, 1940, p. 71–74
  0.5 mg/kg i.v.: $ED_{50}$ In vitro 1. Allergically-induced histamine release from mast cells (rat)
  Lit.: J. Immunol. Meth. 30, 1979, p. 55–68
  0.7 μmol/l: $IC_{50}$
2. Lipopolysaccharide-induced interleucin-1 production of monocytes (man)
  Lit.: Cell. Immunol. 125, 1990, p. 142–150
  4.5 μmol/l: $IC_{50}$
3. Platelet-activating factor (Paf)-induced oxygen radical release from alveolar macrophages (guinea pig)
  Lit.: J. Lipid Med. 5, 1991, p. 13–22
  6.1 μmol/l: $IC_{50}$
4. 5-Lipoxygenase inhibition in peritoneal macrophages (rat)
  12 μmol/l: $IC_{50}$ The compound with the name 4,5-dihydro-8-hydroxy-4-oxo-pyrido [3,2-e]-pyrrolo[1,2-a]pyrazine displays an $IC_{50}$ of 32.2 μmol/l in phosphordiesterase inhibition. In the same experiment, the compound according to Example 98 shows an $IC_{50}$ of 15.1 μmol/l.

The compound with number D 20169 has an $IC_{50}$ value of 7.34 μmol/l in phosphordiesterase inhibition. Examples for the compounds of Formula I Example 1 (number D 21247)

5-Ethyl-8-[3-(N-cyclohexyl-N-methylcarbamoyl)-propyloxy]-4,5-dihydro-4-oxo-pyrido[3,2-e]-pyrrolo[1,2-a]pyrazine

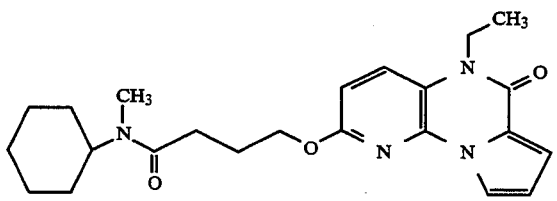

A suspension of 3.8 g (10 mmol) 8-[3-(N-cyclohexyl-N-methylcarbamoyl)-propyloxy]-4,5-dihydro-4-oxo-pyrido [3,2-e]-pyrrolo[1,2-a]pyrazine in 50 ml dimethylformamide is reacted with stirring under a protective gas atmosphere in portions with 0.26 g (11 mmol) 80 percent sodium hydride in white oil. When addition has been completed, the mixture is stirred at room temperature for 2 hours and a solution of 1.2 g (11 mmol) ethyl bromide in 5 ml dimethylformamide is subsequently added dropwise with stirring and protective gas atmosphere (nitrogen, argon). When addition has been completed, the mixture is stirred for 2 hours at 80° C., allowed to cool to room temperature and filtered to remove insoluble constituents. After concentration in a vacuum and recrystallization from 2-propanol, 3.5 g (85 % of theory) of the stated reaction product are obtained in the form of colorless crystals, M.P. 156°–157° C. The starting compound ($R_1$=H) is for example obtained as follows: 4.0 g (20 mmol)4,5-Dihydro-8-hydroxy-4-oxo-pyrido[3,2-e]-pyrrolo [1,2-a]pyrazine are reacted with 3.9 g (20 mmol) 4-bromobutyric acid ethyl ester. Etherification of the 8-hydroxy group is carried out by analogy with the mode of working described for the preparation of starting materials. 1.5 g 4,5-Dihydro-8-[3-ethoxycarbonylpropyloxy]-4-oxo-pyrido[3,2-e]pyrrolo[1,2a]pyrazine are obtained as colorless crystals (MP 148°–151° C).

A mixture of 9.5 g of the so obtained 3-ethoxycarbonyl compound (30 mmol), 11.2 g (0.2 mmol) potassium hydroxide and 250 ml methanol/water mixture (4:1) is heated with stirring for 16 hours under reflux. After cooling to room temperature the mixture is acidulated with stirring with concentrated hydrochloric acid, precipitated solid matter is suctioned off and the mixture washed neutral with water. The product is then extracted in acetone, suctioned off again after cooling and dried in a vacuum. 7.9 g4,5-Dihydro-8-[3-carboxypropyloxy]-4-oxo- pyrido[3,2-e]pyrrolo [1,2-a]pyrazine are obtained as colorless crystals (MP 268°–272° C).

3.2 g (25 mmol) oxalyl chloride are added dropwise to a mixture of 5.8 g (20 mmol) of the so obtained 3-carboxy compound, 0.5 ml dimethylformamide and 300 ml toluene with stirring and exclusion of moisture and stirring continued for 2 hours at 50°–55° C. The toluene is then distilled off in a vacuum, the residue is taken up in 50 ml tetrahydrofuran and the mixture is again concentrated in a vacuum until dryness. The distillation residue is taken up in 100 ml tetrahydrofuran.

The resulting suspension is dropped with stirring and exclusion of moisture at 0°–5° C. into a mixture of 5.6 g (50 mmol) N-methylcyclohexylamine and 2.6 g (25 mmol) sodium carbonate in 120 ml tetrahydrofuran/water mixture (25:1). When addition is complete, the mixture is heated to room temperature with stirring and allowed to post-react overnight. Insoluble constituents are filtered off, the filtrate is concentrated in a vacuum and the residue is recrystallized from 2-propanol. 6.1 g 8-[3-(N-cyclohexyl-N-methylcarbamoyl)-propyloxy]4,5-dihydro-4-oxo-pyrido[3,2-e]pyrrolo[1,2-a]pyrazine are obtained as colorless crystals, M.P. 192°–193° C).

The following starting materials are obtained by analogy with the above described hydrolytic removal of an alkoxy group (ethoxy group):
4,5-Dihydro-8-[4-carboxybutyloxy]-4-oxo-pyrido[3,2-e]pyrrolo[1,2-a]pyrazine (number D 20098).

A mixture of 9.9 g (30 mmol) 4,5-dihydro-8-[4-ethoxycarbonylbutyloxy]-4-oxo-pyrido[3,2-e]pyrrolo[1,2-a]pyrazine, 11.2 g (0.2 mol) potassium hydroxide and 250 ml methanol/water mixture (4:1) are reacted and worked up as described above. After drying in a vacuum, 8.5 g of substance D 20098 are obtained as colorless crystals, M.P. 229°–233° C.

4,5-Dihydro-8-[carboxymethoxy]-4-oxo-pyrido[3,2-e]pyrrolo[1,2-a]pyrazine (number D 20097).

A mixture of 8.6 g (30 mmol) 4,5-dihydro-8-[ethoxycarbonylmethoxy]-4-oxo-pyrido[3,2-e]pyrrolo[1,2-a]pyrazine, 11.2 g (0.2 mol) potassium hydroxide and 250 ml methanol/water mixture (4:1) are reacted and worked up as described above. After drying in a vacuum 7.3 g of substance D 20097 are obtained as colorless crystals, M.P. 296°–298° C.

The following starting materials are for example obtained by analogy with the above described amination (conversion of the carbonyl group of a carboxy compound into the chlorocarbonyl group and subsequent reaction with N-methyl-cyclohexylamine):

8-[3-(4-morpholinylcarbonyl)-propyloxy]-4,5-dihydro-4-oxo-pyrido[3,2-e]-pyrrolo[1,2-a]pyrazine (number D 19897).

5.4 g of substance D 19897 are obtained from 5.8 g (20 mmol) 4,5-dihydro-8-[3-carboxypropyloxy]-4-oxo-pyrido[3,2-e]pyrrolo[1,2-a]pyrazine and 4.4 g (50 mol) morpholine as colorless crystals, M.P. 205°–207° C.

8-[3-(1-piperidinylcarbonyl)-propyloxy]-4,5-dihydro-4-oxo-pyrido[3,2-e]-pyrrolo[1,2-a]pyrazine (number D 19898).

5.5 g of substance D 19898 are obtained from 5.8 g (20 mmol) 4,5-dihydro-8-[3-carboxypropyloxy]-4-oxo-pyrido [3,2-e]pyrrolo[1,2-a]pyrazine and 4.3 g (50 mol) piperidine as colorless crystals, M.P. 190°–192° C.

8-[3-(N-fluorobenzyl)-carbamoyl)-propyloxy]-4,5-dihydro-4-oxo-pyrido[3,2-e]-pyrrolo[1,2-a]pyrazine (number D 19899).

6.1 g of substance D 19899 are obtained from 5.8 g (20 mmol) 4,5-dihydro-8-[3-carboxypropyloxy]-4-oxo-pyrido[3,2-e]pyrrolo[1,2-a]pyrazine and 6.3 g (50 mol) 4-fluorobenzylamine as colorless crystals, M.P. 246°–248° C.

8-[3-(N-benzylcarbamoyl)-propyloxy]-4,5-dihydro-4-oxo-pyrido[3,2-e]-pyrrolo[1,2-a]pyrazine (number D 19918).

5.5 g of substance D 19918 are obtained from 5.8 g (20 mmol) 4,5-dihydro-8-[3-carboxypropyloxy]-4-oxo-pyrido[[3,2-e]pyrrolo[1,2-a]pyrazine and 5.6 g (50 mol) benzylamine as colorless crystals, M.P. 232°–234° C.

-[2-(N-cyclohexyl-N-methylcarbamoyl)-methoxy]-4,5-dihydro-4-oxo-pyrido[3,2-e]-pyrrolo[1,2-a]pyrazine (number D 20099).

5.1 g of substance D 20099 are obtained from 5.2 g (20 mmol) 4,5-dihydro-8-[carboxymethoxy]-4-oxo-pyrido[3,2-e]pyrrolo[1,2-a]pyrazine and 5.6 g (50 mol) N-methylcyclohexylamine as colorless crystals, M.P. 208°–209° C.

8-[(4-morpholinylcarbonyl)-methoxy]-4,5-dihydro-4-oxo-pyrido[3,2-e]-pyrrolo[1,2-a]pyrazine (number D 20115).

5.0 g of substance D 20115 are obtained from 5.2 g (20 mmol) 4,5-dihydro-8-[carboxymethoxy]-4-oxo-pyrido[3,2-e]pyrrolo[1,2-a]pyrazine and 4.4 g (50 mol) morpholine as colorless crystals, M.P. 263°–264° C.

8-[(1-piperidinylcarbonyl)-methoxy]-4,5-dihydro-4-oxo-pyrido[3,2-e]-pyrrolo[1,2-a]pyrazine (number D 20172).

5.0 g of substance D 20172 are obtained from 5.2 g (20 mmol) 4,5-dihydro-8-[carboxymethoxy]-4-oxo-pyrido[3,2-e]pyrrolo[1,2-a]pyrazine and 4.3 g (50 mol) piperidine as colorless crystals, M.P. 214°–216° C.

8-[(N-benzylcarbamoyl)-methoxy]-4,5-dihydro-4-oxo-pyrido[3,2-e]-pyrrolo[1,2-a]pyrazine (number D 20170).

5.7 g of substance D 20170 are obtained from 5.2 g (20 mmol) 4,5-dihydro-8-[carboxymethoxy]-4-oxo-pyrido[3,2-e]pyrrolo[1,2-a]pyrazine and 5.4 g (50 mol) benzylamine as colorless crystals, M.P. 280°–281° C.

8-[(N-fluorobenzyl)-carbamoyl)-methoxy]-4,5-dihydro-4-oxo-pyrido[3,2-e]-pyrrolo[1,2-a]pyrazine (number D 20173).

5.9 g of substance D 20173 are obtained from 5.2 g (20 mmol) 4,5-dihydro-8-[carboxymethoxy]-4-oxo-pyrido[3,2-e]pyrrolo[1,2-a]pyrazine and 6.3 g (50 mol) 4-fluorobenzylamine as colorless crystals, M.P. 301°–304° C.

8-[4-(N-cyclohexyl)-N-methylcarbamoyl)-butyloxy]-4,5-dihydro-4-oxo-pyrido[3,2-e]-pyrrolo[1,2-a]pyrazine (number D 20169).

5.7 g of substance D 20169 are obtained from 6.0 g (20 mmol) 4,5-dihydro-8-[4-carboxybutyloxy]-4-oxo-pyrido[3,2-e]pyrrolo[1,2-a]pyrazine and 5.6 g (50 mol) N-methylcyclohexylamine as colorless crystals, M.P. 130°–133° C.

8-[4-(N-benzylcarbamoyl)-butyloxy]-4,5-dihydro-4-oxo-pyrido[3,2-e]-pyrrolo[1,2-a]pyrazine (number D 20171).

5.9 g of substance D 20171 are obtained from 6.0 g (20 mmol) 4,5-dihydro-8-[4-carboxybutyloxy]-4-oxo-pyrido[3,2-e]pyrrolo[1,2-a]pyrazine and 5.4 g (50 mol) benzylamine as colorless crystals, M.P. 238°–240° C.

8-[4-(4-morpholinylcarbonyl)-butyloxy]-4,5-dihydro-4-oxo-pyrido[3,2-e]-pyrrolo[1,2-a]pyrazine (number D 20211).

5.5 g of substance D 20211 are obtained from 6.0 g (20 mmol) 4,5-dihydro-8-[4-carboxybutyloxy]-4-oxo-pyrido[3,2-e]pyrrolo[1,2-a]pyrazine and 4.4 g (50 mol) morpholine as colorless crystals, M.P. 199°–202° C.

8-[4-(1-piperidinylcarbonyl)-butyloxy]-4,5-dihydro-4-oxo-pyrido[3,2-e]-pyrrolo[1,2-a]pyrazine (number D 20212).

5.5 g of substance D 20212 are obtained from 6.0 g (20 mmol) 4,5-dihydro-8-[4-carboxybutyloxy]-4-oxo-pyrido[3,2-e]pyrrolo[1,2-a]pyrazine and 4.3 g (50 mol) piperidine as colorless crystals, M.P. 191°–193° C.

Example 2a

1-Chloro-5-hydroxy-4,5-dihydro-4-oxo-pyrido[3,2-e]pyrrolo[1,2-a]pyrazine

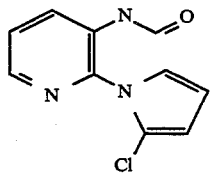

A solution of 50 g (178 mmol) 2-[1-(2-ethoxycarbonyl-4-hydroxy)-pyrrolidinyl]-3-nitropyridine (prepared from 2-chloro-3-nitropyridine and hydroxyproline ethyl ester; see preparation of starting materials) and 38 g ammonium chloride (0.7 mmol in 1200 ml ethanol/water mixture (1:1) are mixed in portions with 46.5 g zinc dust with stirring. During this procedure the temperature gradually rises to 40° C. When addition has been completed, the mixture is stirred for 1 hour at 40°–45° C. After cooling to room temperature the solution is filtered and the remaining solid substance is extracted four times with, in each case, 200 ml dimethylacetamide. The combined extracts are concentrated in a vacuum and the remaining residue is added with stirring to ethanolic hydrochloric acid. After standing overnight at 0°–4° C. the mixture is suctioned off, the solid substance is taken up in 1.5 liters hot methanol and stirred for 20 days with passage of air at room temperature. The crystalline precipitate is suctioned off and rewashed with methanol. 11.5 g (27% of theory) of the stated reaction product is obtained after recrystallization from dioxan as beige-colored crystals, M.P. 265°–267° C.

Example 2b (number D 19529)

Formula as for Example 2a, but without the chlorine in the 1 position.
Preparation: by analogy with Example 2a.
M.P. 235°–236° C.

Example 3 (number D 19696)

1-Chloro-5-benzyloxy-4,5-dihydro-4-oxo-pyrido[3,2-e]pyrrolo[1,2-a]pyrazine

A suspension of 2.4 g (10 mmol) 1-chloro-5-hydroxy-4,5-dihydro-4-oxo-pyrido[3,2-e]pyrrolo[1,2-a]pyrazine (Example 2) in 50 ml dimethylformamide is mixed with stirring under a protective gas atmosphere in portions with 0.26 g (11 mmol) 80 percent sodium hydride in white oil. When addition has been completed the mixture is stirred for 2 hours at room temperature and a solution of 2.0 g (11 mmol) benzylbromide in 5 ml dimethylformamide is then added dropwise thereto with stirring under a protective gas atmosphere. When addition has been completed, the mixture is stirred for 2 hours at 80° C., allowed to cool to room temperature and then filtered to remove insoluble constituents. 1.9 g (58% of theory) of the cited reaction product are obtained after concentration in a vacuum and recrystallization from acetone as colorless crystals.
M.P. 179°–180° C.

Example 4a (number D 19668)

1-Chloro-5-(N,N-diethylcarbamoyloxy)-4,5-dihydro-4-oxo-pyrido[3,2-e]pyrrolo[1,2-a]pyrazine A suspension of 2.4 g (10 mmol) 1-chloro-5-hydroxy-4,5-dihydro-4-oxo-pyrido[3,2-e]pyrrolo [1,2-a]pyrazine (Example 2) in 50 ml dimethylformamide is reacted with 1.5 g (11 mmol) N,N-diethylcarbamoylchloride by analogy with Example 3. 1.1 g (33% of theory) of the stated reaction product are obtained after recrystallization from acetic ester as colorless crystals. M.P. 173°–175° C.

Example 4b (number D 19537)

5-Morpholinocarbonyloxy-4,5-dihydro-4-oxo-pyrido-[3,2-e]pyrrolo[1,2-a]pyrazine
M.P. 176°–177° C.

Example 4c (number D 19591)

1-Chloro-5-ethoxycarbonyloxy-4,5-dihydro-4-oxo-pyrido[3,2-e]pyrrolo[1,2-a]pyrazine
M.P. 163°–165° C.

Example 4d (number D 19621)

1-Chloro-5-dimethylaminocarbonyloxy-4,5-dihydro-4-oxo-pyrido[3,2-e]pyrrolo[1,2-a]pyrazine
M.P. 210°–211° C.

Example 4e (number D 19629)

1-Chloro-5-morpholinocarbonyloxy-4,5-dihydro-4-oxo-pyrido[3,2-e]pyrrolo[1,2-a]pyrazine
M.P. 204°–205° C.

Example 4f (number D 19669)

1-Chloro-5-acetoxy-4,5-dihydro-4-oxo-pyrido[3,2-e]pyrrolo[1,2-a]pyrazine
M.P. 196°–198° C.

Example 4g (number D 19700)

1-Chloro-5-propene(2)-oxy-4,5-dihydro-4-oxo-pyrido[3,2-e]pyrrolo[1,2-a]pyrazine
M.P. 104°–106° C.

Example 4h (number D 19711)

1-Chloro-5-propine-(2)-oxy-4,5-dihydro-4-oxo-pyrido[3,2-e]pyrrolo[1,2-a]pyrazine
M.P. 205°–207° C.

The compounds according to Examples 4b to 4f are prepared by analogy with Example 4a.

Examples 5 to 10

Examples for compounds of formula I where $R_1$ is $C_1$–$C_6$-halogenalkyl.

A suspension of 0.5 mol of a compound of Formula I, where $R_1$ is hydrogen, in 1000 ml dimethylformamide (or dimethylacetamide or N-methylpyrrolidone) is mixed in portions with stirring and exclusion of moisture with 16.5 to 22.5 g (0.55–0.75 mol) 80 percent sodium hydride in white oil. When addition has been completed, the mixture is stirred for 2 hours at room temperature and the reaction mixture is subsequently added dropwise into dimethylformamide (or dimethylacetamide or N-methylpyrrolidone) with stirring under a protective gas atmosphere to a solution of 1–10 mol of the corresponding 1-bromo-ω-chloroalkanes or 1,ω-dihalogenalkane, where both halogen atoms are the same. When addition has been completed the mixture is stirred for 3 hours at room temperature and then insoluble constituents filtered off. After concentration in a vacuum and recrystallization from acetonitrile the pure ω-halogenalkyl derivatives or mixtures of the corresponding ω-bromo or ω-chloroalkyl compounds, depending on the 1,ω-dihalogen alkane used, are obtained, the ratio of which can be determined from 1H-NMR data. These halogenalkyl compounds or the corresponding mixtures may be used for further reactions without further working up.

Example 5 (number RD 680/B16066)

4:1 mixture of 5-(2-chloroethyl)- and 5-(2-bromoethyl)-4,5-dihydro-8-methoxy-4-oxo-pyrido[3,2-e]pyrrolo[1,2-a]pyrazine:

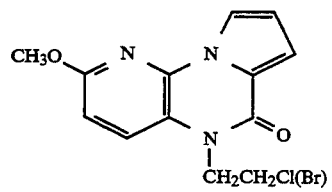

Colorless to beige crystals. The mixture melts at 172°–173° C.
Yield: 52% of theory.

Example 6 (number RD 537/B16017)

3:2 mixture of 5-(3-bromopropyl)- and 5-(3-chloropropyl)-4,5-dihydro-8-methoxy-4-oxo-pyrido[3,2-e]pyrrolo[1,2-a]pyrazine.
Colorless to beige crystals. M.P. 105°–107° C.
Yield: 68% of theory.

Example 7 (number RD 541/UE 3)

9:1 mixture of 5-(3-chloropropyl)- and 5-(3-bromopropyl) 4,5-dihydro-4-oxo-pyrido[3,2-e]pyrrolo[1,2-a]pyrazine
Colorless to beige crystals. M.P. 144°–145° C.
Yield: 72% of theory.

Example 8 (number RD 781/MB8)

5-(6-Bromohexyl)-4,5-dihydro-4-oxo-pyrrolo[1,2-a]quinoxalin one

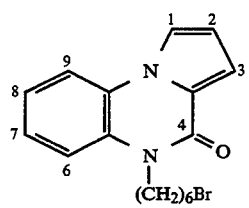

Colorless to beige crystals. M.P. 83°–85° C.
Yield: 77% of theory.

Example 9 (number RD 789/T7627)

3:2 mixture of 5-(4-bromobutyl- and 5-(4-chlorobutyl-4,5-dihydro-8-methyl-4-oxo-pyrrolo[1,2-a]quinoxalinone
Colorless to beige crystals. M.P. 87°–88° C.
Yield: 49% of theory.

Example 10 (number RD 790/T7632)

7:3 mixture of 5-(3-chloro-2-methylpropyl)- and 5-(3-bromo-2-methylpropyl)-4,5-dihydro-4-oxo-pyrrolo[1,2-a]quinoxalinone
Colorless to beige crystals. M.P. 122°–124° C.
Yield: 53% of theory.

Examples 11–97

The compounds of these examples are set out in the following general formula and the corresponding Table 1.

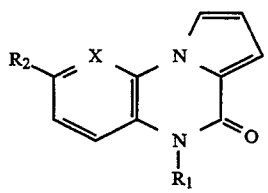

TABLE 1

| Example No. | X | $R_1$ | $R_2$ | F °C. | Number |
|---|---|---|---|---|---|
| 11 | N | $(C_6H_5)_2CH-N\diagup\diagdown N-(CH_2)_3-$ | H | 225–228 Dihydrochloride | D 20896 |
| 12 | N | $(4-F-C_6H_4)_2CH-N\diagup\diagdown N-(CH_2)_3-$ | H | 173–175 | D 20897 |
| 13 | N | $(C_6H_5)_2CH-N\diagup\diagdown N-(CH_2)_3-$ | $\begin{array}{c}CH_3\\|\\H-\langle\rangle-N-CO-(CH_2)_3-O-\end{array}$ | 192–195 Dihydrochloride | D 21280 |
| 14 | N | $(C_6H_5)_2CH-N\diagup\diagdown N-(CH_2)_3-$ | " | 178–182 Dihydrochloride | D 21524 |
| 15 | N | 2-methoxyphenyl-piperazinyl-$(CH_2)_3-$ | " | 184–188 Hydrochloride | D 21525 |
| 16 | N | $(4-F-C_6H_4)_2CH-N\diagup\diagdown N-(CH_2)_3-$ | " | 200 Dihydrochloride | D 21616 |
| 17 | N | 2-methoxyphenyl-piperazinyl-$(CH_2)_3-$ with CH$_3$ | H | 204–209 Hydrochloride | D 21617 |

TABLE 1-continued

| Example No. | X | R₁ | R₂ | F °C. | Number |
|---|---|---|---|---|---|
| 18 | CH | 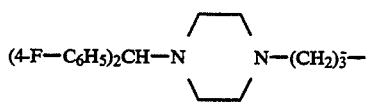 (4-F—C₆H₅)₂CH—N\_/N—(CH₂)₃— | H | 220–224 Dihydrochloride | D 21157 |
| 19 | N | 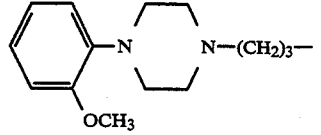 | H | 213–216 Dihydrochloride | D 21010 |
| 20 | CH | 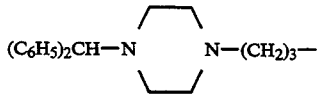 (C₆H₅)₂CH—N\_/N—(CH₂)₃— | H | 228–230 Dihydrochloride | D 21400 |
| 21 | CH | 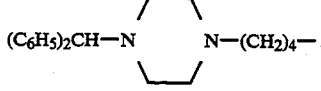 (C₆H₅)₂CH—N\_/N—(CH₂)₄— | H | 243–250 Dihydrochloride | D 21402 |
| 22 | CH | 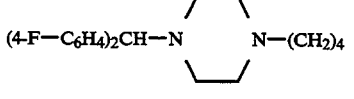 (4-F—C₆H₄)₂CH—N\_/N—(CH₂)₄ | H | 165–167 | D 21401 |
| 23 | CH | 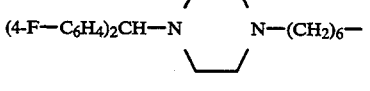 (4-F—C₆H₄)₂CH—N\_/N—(CH₂)₆— | H | 206–212 Dihydrochloride | D 21619 |
| 24 | CH | 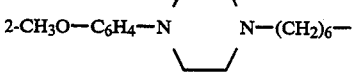 2-CH₃O—C₆H₄—N\_/N—(CH₂)₆— | H | 172–179 Dihydrochloride | D 21618 |
| 25 | CH | 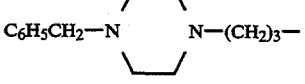 C₆H₅CH₂—N\_/N—(CH₂)₃— | H | 229–232 Dihydrochloride | D 21117 |
| 26 | N |  C₆H₅)₂CH—N\_/N—(CH₂)₃— | CH₃O | 220–226 Dihydrochloride 1 Mol H₂O | D 20971 |
| 27 | N | 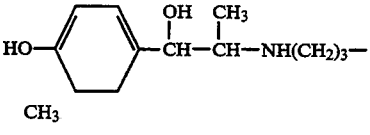 | CH₃O | 218–219 Hydrochloride | D 21237 |
| 28 | N | 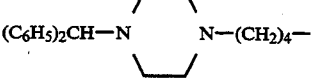 (C₆H₅)₂CH—N\_/N—(CH₂)₄— | CH₃O | 175 | D 21271 |
| 29 | N | 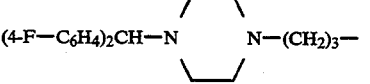 (4-F—C₆H₄)₂CH—N\_/N—(CH₂)₃— | CH₃O | 216–219 Dihydrochloride 1 Mol H₂O | D 20972 |

TABLE 1-continued

| Example No. | X | R₁ | R₂ | F °C. | Number |
|---|---|---|---|---|---|
| 30 | N | C₆H₅)₂CH—N⟨piperazine⟩N—(CH₂)₂— | CH₃O | 180 Dihydrochloride | D 21206 |
| 31 | N | C₂H₅OCO—⟨piperidine-4⟩N—(CH₂)₃— · HBr | CH₃O | 180 Hydrobromide | D 20898 |
| 32 | N | C₆H₅—N⟨piperazine⟩N—(CH₂)₃— | CH₃O | 224–226 Dihydrochloride 1 Mol H₂O | D 20944 |
| 33 | N | C₆H₅—⟨piperidine-4⟩N—(CH₂)₃— | CH₃O | 241–245 Hydrochloride 1 Mol H₂O | D 20973 |
| 34 | N | 4-F—C₆H₅—CH₂—NH—(CH₂)₃— · HBr | CH₃O | 206 Hydrobromide | D 20974 |
| 35 | N | 2-CH₃O-C₆H₄—N⟨piperazine⟩N—(CH₂)₃— | CH₃O | 143–146 Dihydrochloride | D 21008 |
| 36 | N | C₆H₅—CH₂—N⟨piperidine with ring N⟩(CH₂)₃— · HBr | CH₃O | 188–191 Hydrobromide | D 21009 |
| 37 | N | C₆H₅—(CH₂)₃—NH(CH₂)₃— | CH₃O | 173–174 Hydrochloride | D 21045 |
| 38 | N | C₆H₅—CH₂—NH(CH₂)₃— | CH₃O | 221–223 Hydrochloride | D 21046 |
| 39 | N | cyclohexyl—NH—(CH₂)₃— | CH₃O | 233–235 Hydrochloride | D 21081 |
| 40 | N | imidazole-N—(CH₂)₃— | CH₃O | 197–199 Hydrochloride | D 21088 |
| 41 | N | HO—⟨piperidine-4⟩N—(CH₂)₃— | CH₃O | 103–105 | D 21089 |
| 42 | N | 4-CF₃—C₆H₄—N⟨piperazine⟩N—(CH₂)₃— | CH₃O | 203–205 | D 21090 |

TABLE 1-continued

| Example No. | X | R₁ | R₂ | F °C. | Number |
|---|---|---|---|---|---|
| 43 | N | 4-CH₃—C₆H₄—N(piperazine)—(CH₂)₃— | CH₃O | 229–231 Hydrochloride | D 21159 |
| 44 | N | 4Cl—C₆H₄CH₂—N(piperazine)—(CH₂)₃— | CH₃O | 245–248 Dihydrochloride | D 21205 |
| 45 | N | 3,4-methylenedioxy-C₆H₃—CH₂—N(piperazine)—(CH₂)₃— | CH₃O | 225–228 Dihydrochloride | D 21207 |
| 46 | N | HO—(CH₂)₃—N(piperazine)—(CH₂)₃— | CH₃O | 226–228 Dihydrochloride | D 21236 |
| 47 | N | 3-hydroxypiperidin-1-yl—(CH₂)₃— | CH₃O | 225–228 Hydrochloride | D 21272 |
| 48 | N | 2-CN-C₆H₄—N(piperazine)—(CH₂)₃— | CH₃O | 224–226 Hydrochloride | D 21273 |
| 49 | N | 3,5-Cl₂-C₆H₃—N(piperazine)—(CH₂)₃— | CH₃O | 254–256 Hydrochloride | D 21387 |
| 50 | N | H₂N—(CH₂)₃— | CH₃O | 261–263 Hydrochloride | D 21158 |
| 51 | N | morpholino—(CH₂)₂—NH(CH₂)₃ | CH₃O | 215–220 Dihydrochloride | D 21161 |
| 52 | N | C₆H₅—CH(OH)—CH(CH₃)—NH(CH₂)₃— | CH₃O | 223–225 Hydrochloride L-Erythro-Form | D 21160 |
| 53 | N | C₆H₅CH₂—N(piperidine-4-yl)—NH(CH₂)₃— | CH₃O | 259–261 Dihydrochloride | D 21162 |
| 54 | N | 2-OCH₃-C₆H₄—N(piperazine)—(CH₂)₃— | Cl | 228 Hydrochloride | D 21155 |

TABLE 1-continued

| Example No. | X | R₁ | R₂ | F °C. | Number |
|---|---|---|---|---|---|
| 55 | N | C₆H₅CH₂—N(piperazine)N—(CH₂)₃— | Cl | 204–208 Dihydrochloride | D 21156 |
| 56 | N | (C₆H₅)₂CH—N(piperazine)N—(CH₂)₃— | Cl | 212–217 Dihydrochloride 1 Mol Water | D 21526 |
| 57 | N | (4F—C₆H₄)CH—N(piperazine)N—(CH₂)₃— | Cl | 208–212 Dihydrochloride | D 21527 |
| 58 | N | C₆H₅CH₂— | CH₃O | 126–127 | D 18540 |
| 59 | N | C₆H₅(CH₂)₂— | CH₃O | 112–114 | D 18541 |
| 60 | N | C₆H₅(CH₂)₃— | CH₃O | 98–99 | D 18542 |
| 61 | N | CH₃CH₂— | CH₃O | 106–112 | D 18688 |
| 62 | N | CH₃(CH₂)₂— | CH₃O | 88–89 | D 18689 |
| 63 | N | CH₃(CH₂)₃— | CH₃O | 83–86 | D 18690 |
| 64 | N | C₆H₅CH₂— | H | 138–141 | D 18697 |
| 65 | N | CH₃— | CH₃O | >160 (disintegration) | D 18999 |
| 66 | N | C₆H₅CH₂— | H | >176 (disintegration) | D 19000 |
| 67 | N | C₆H₅(CH₂)₂— | H | >131 (disintegration) | D 19001 |
| 68 | CH | C₆H₅(CH₂)₃— | H | >85 (disintegration) | D 19002 |
| 69 | CH | C₆H₅CO— | H | >180 (disintegration) | D 19003 |
| 70 | N | C₆H₅CO— | H | >179 (disintegration) | D 19004 |
| 71 | N | (CH₃)₂N—(CH₂)₂— | CH₃O | 246–247 Hydrochloride | D 19038 |
| 72 | N | (CH₃)₂N—(CH₂)₂— | H | 292–293 Hydrochloride | D 19126 |
| 73 | CH | (CH₃)₂N—(CH₂)₂— | H | 285–287 Hydrochloride | D 19127 |
| 74 | N | (CH₃)₂N—(CH₂)₃— | CH₃O | 229–231 Hydrochloride | D 19128 |
| 75 | N | (CH₃)₂N—(CH₂)₃— | H | 276–278 Hydrochloride | D 19129 |
| 76 | CH | (CH₃)₂N—(CH₂)₃— | H | 208–211 Hydrochloride | D 19130 |
| 77 | N | (C₂H₅)₂N(CH₂)₂— | CH₃O | 217–219 Hydrochloride | D 19131 |
| 78 | N | (C₂H₅)₂N(CH₂)₂— | H | 208–211 Hydrochloride | D 19132 |
| 79 | CH | (C₂H₅)₂N(CH₂)₂— | H | 202–205 Hydrochlorlde | D 19133 |
| 80 | N | (C₂H₅)₂N(CH₂)₃— | H | 210–220 Hydrochloride | D 19134 |
| 81 | CH | (C₂H₅)₂N(CH₂)₃— | H | 175–177 Hydrochloride | D 19135 |
| 82 | N | (piperidine)N—(CH₂)₃— | H | 218–220 Hydrochloride | D 19136 |
| 83 | CH | (piperidine)N—(CH₂)₃— | H | 188–191 Hydrochloride | D 19137 |
| 84 | N | (C₂H₅)₂N—(CH₂)₃ | CH₃O | 217–218 Hydrochloride | D 19218 |
| 85 | CH | (piperidine)N—(CH₂)₂— | H | 260–263 Hydrochloride | D 19219 |
| 86 | N | (CH₃)₂N—CH₂—CH(CH₃)— | CH₃O | 217–218 Hydrochloride | D 19221 |

TABLE 1-continued

| Example No. | X | R₁ | R₂ | F °C. | Number |
|---|---|---|---|---|---|
| 87 | N | $(CH_3)_2N-CH_2-CH(CH_3)-$ | H | 284–290 Hydrochloride | D 19223 |
| 88 | N | morpholino-$(CH_2)_2-$ | H | 257–258 Hydrochloride | D 19224 |
| 89 | N | morpholino-$(CH_2)_2-$ | $CH_3O$ | 213–216 Hydrochloride | D 19225 |
| 90 | N | 1-methylpyrrolidin-2-yl-$(CH_2)_2-$ | H | 232–233 Hydrochloride | D 19226 |
| 91 | CH | $(CH_3)_2N-CH_2-CH(CH_3)-$ | H | 268–270 Hydrochloride | D 19324 |
| 92 | CH | morpholino-$(CH_2)_2-$ | H | 227–229 Hydrochloride | D 19325 |
| 93 | N | 1-methylpyrrolidin-2-yl-$(CH_2)_2-$ | H | 181–184 Hydrochloride | D 19326 |
| 94 | N | $CH_3-CH(OH)-CH_2-$ | H | 181–184 | D 19327 |
| 95 | N | $CH_2(OH)-CH(OH)-CH_2-$ | $CH_3O$ | 160–164 | D 19328 |
| 96 | N | $CH_2(OH)-CH(OH)-CH_2-$ | H | 164–166 | D 19456 |
| 97a | N | $CH\equiv C-CH_2$ | $CH\equiv C-CH_2O$ | 218–220 | D 19800 |
| 98 | N | H | $-O-(CH_2)_3-C(=O)-N(H)(CH_3)$ | 262–264 | D 20239 |
| 99 | N | H | diphenylmethyl-piperazinium $Cl^\ominus$ | >250 | D 20400 |

General instructions for the preparation of the compounds of Table 1.

A solution of 2.7 g (10 mmol) of a 9:1 mixture of 5-(3-chloropropyl- and 5-(3-bromopropyl)-4,5-dihydro-4-oxo-pyrido[3,2-e]pyrrolo[1,2-a]pyrazine (Example 7), 2.6 g (10.5 mmol) 1-diphenylmethylpiperazine and 1.1 g (11 mmol) triethylamine in 50 ml dimethylformamide is heated with stirring under a protective gas atmosphere for 3 hours to 120°–130° C. After cooling to room temperature the reaction mixture is evaporated to dryness and the residue is taken up in 150 ml dichloromethane. The dichloromethane phase is extracted in each case once with 30 ml 2N hydrochloric acid and 30 ml 2N sodium hydroxide solution and then washed neutral three times with, in each case, 40 ml water. After drying with sodium sulfate, the dichloromethane phase is concentrated in a vacuum, the residue is taken up in 80 ml ethanol and brought to crystallization by addition of ethanolic hydrochloric acid. The crystallizate obtained is suctioned off, rewashed with methanol and dried in a vacuum.

Starting materials for Examples 13, 14 and 15 are in each case a 2:1 mixture of 5-(3-bromopropyl)- and 5-(3-chloropropyl) -8-[3-(N-cyclohexyl-N-methyl-carbamoyl)propyloxy]-4,5-dihydro-4-oxo-pyrido[3,2-e]pyrrolo[1,2-a]pyrazine and 1 benzylpiperazine (Example 13), 1-diphenylmethylpiperazine (Example 14) and 1(2-methoxyphenyl piperazine) (Example 15).

In Example 17, the starting compounds are a 1:1 mixture of 5-(3-bromopropyl)- and 5-(3-chloropropyl)-8-[3-(N-cyclohexyl-N-methylcarbamoyl)-propyloxy]-4,5-dihydro-4-oxo-pyrido[3,2-e]pyrrolo[1,2-a]pyrazine (Example 10) and 1-(2-methoxyphenyl) piperazine.

The starting compound for Example 16 is:

For Examples 19 and 20 the one starting component is in each case a 4:1 mixture of 5-(3-chloropropyl)- and 5-(3-bromopropyl)-4,5-dihydro-4-oxo-pyrrolo[1,2-a]quinoxalinone and the other 1-(2-methoxyphenyl)-piperazine (Example 19) and 1-diphenylmethylpiperazine (Example 20). For Examples 21 and 22 the one starting component is in each case a 3:2 mixture of 5-(6-bromohexyl)-4,5-dihydro-4-oxo-pyrrolo[1,2-a]quinoxalinone (see Example 9) and the other is 1-diphenylmethyl piperazine (Example 21) or 1-(di-(4-fluorophenyl)-methyl piperazine.

For Examples 23 and 24 the one starting component is in each case 5-(6-bromohexyl)-4,5-dihydro-4-oxo-pyrrolo[1,2-a]quinoxalinone (see Example 8) and the other 1-(di-C4-fluorophenyl)-methyl)-piperazine (Example 23) or 1-(2-methoxyphenyl)-piperazine (Example 24).

It is of course also possible to use other 5-halogenalkyl mixtures apart from those listed above and also the pure 5-halogenalkyl compounds.

What is claimed is:

1. Compounds of the formula

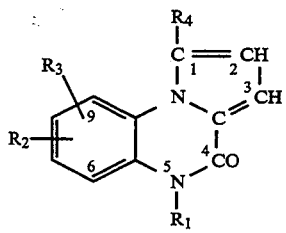

where the benzo ring can also contain a nitrogen atom instead of a CH group either in position 6, 7, 8 or 9 and the radicals $R_1$, $R_2$, $R_3$ and $R_4$ have the following meanings:

$R_1$: $C_2$-$C_6$-alkenyl, $C_2$-$C_6$-alkynyl, hydroxy, $C_1$-$C_6$-alkoxy, $C_3$-$C_6$-alkenyloxy, $C_3$-$C_6$-alkynyloxy, $C_2$-$C_6$-alkanoyloxy, benzoyloxy, morpholinocarbonyloxy, $C_1$-$C_6$-alkyloxycarbonyloxy, $C_1$-$C_6$-alkylaminocarbonyloxy, $C_1$-$C_6$-dialkylaminocarbonyloxy or the group -Alk-A where Alk: is $C_1$-$C_6$-alkyl, $C_2$-$C_6$-hydroxyalkyl or $C_3$-$C_6$-cycloalkyl and the symbol A represents:

1) Hydrogen, halogen, hydroxy, $C_1$-$C_6$-alkoxy, $C_2$-$C_6$-alkanoyloxy, phenyl;

2) —$NHR_5$, —$NR_5R_6$, $NR_5R_6R_7$, pyridylamino, imidazolyl, pyrrolidinyl, N—$C_1$-$C_6$-alkylpyrrolidinyl, piperidylamino, N-(phenyl-$C_1$-$C_4$-alkyl)-piperidylamino where $R_5$ and $R_6$ may be the same or different and represent hydrogen, $C_1$-$C_6$-alkyl, $C_3$-$C_7$-cycloalkyl, $C_3$-$C_7$-hydroxycycloalkyl, morpholino-$C_1$-$C_6$-alkyl, phenyl, phenyl-$C_1$-$C_6$-alkyl or phenyl-$C_2$-$C_6$-oxyalkyl, it also being possible for the phenyl radicals in $R_5$ and $R_6$ to be substituted by halogen and $R_7$ is hydrogen or $C_1$-$C_6$-alkyl;

3) The group:

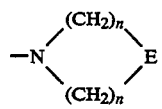

where D is phenyl, $C_1$-$C_6$-alkyl, $C_3$-$C_7$-cycloalkyl, hydroxy, $C_1$-$C_6$-alkoxy, $C_3$-$C_7$-cycloalkyloxy, morpholino, pyrrolidino, piperidino, homopiperidino, piperazino, —$NHR_5$ or —$NR_5R_6$ and $R_5$ and $R_6$ have the meanings given hereinabove;

4) The group:

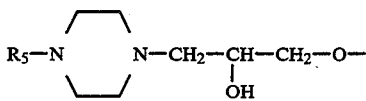

where n can be the integers 1-3 and E represents $CH_2$, oxygen, sulfur, NH, CHOH, CH—$C_1$-$C_6$-alkyloxy, CH—$C_2$-$C_6$-alkanoyloxy, $CHC_6H_5$, CHCOD, CH—$CH_2C_6H_5$, N—$C_1$-$C_6$-alkyl, N—$C_1$-$C_6$-hydroxyalkyl, N—$C_6H_5$, N—$CH_2C_6H_5$, N—$CH(C_6H_5)_2$, N—$(CH_2)_2$—OH, N—$(CH_2)_3$—OH or NCOD and the phenyl radicals ($C_6H_5$) may also be substituted by halogen, $C_1$-$C_6$-alkoxy, trifluoromethyl, $C_1$-$C_6$-alkyl, methylenedioxy or cyan and D has the meanings given hereinabove;

$R_2$ and $R_3$, which may be the same or different: hydrogen, halogen, hydroxy, $C_1$-$C_6$-alkyl, trifluoromethyl, —CN, $C_1$-$C_6$-alkoxy, $C_3$-$C_6$-alkenyloxy, $C_3$-$C_6$-alkynyloxy, —$NHR_5$, —$NR_5R_6$, $NR_5R_6R_7$ (meanings $R_5$, $R_6$, $R_7$ as given hereinabove) or the group -G-Alk-A, where Alk and A have the meanings given hereinabove and G is oxygen, sulfur, NH or $NR_5$ and $R_2$ can also be

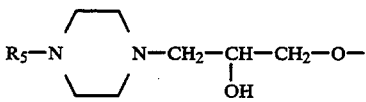

$R_4$: hydrogen or halogen, where $R_1$ can also be hydrogen, when $R_2$ is the group $R_5$—N⟨⟩N—$CH_2$—CH(OH)—$CH_2$—O— and $R_5$ represents phenyl, $C_1$-$C_4$-alkoxyphenyl or diphenylmethyl and $R_3$ and $R_4$ are hydrogen, and their physiologically acceptable acid addition salts and quaternary ammonium salts, with the exception of the compounds of Formula I where $R_1$ is methyl, dimethylaminopropyl, dimethylaminoethyl, morpholinoethyl or pyrrolidinoethyl, $R_2$, $R_3$ and $R_4$ are hydrogen and the benzo ring does not contain a nitrogen atom instead of a CH group.

* * * * *